United States Patent
Pryor et al.

(10) Patent No.: US 7,693,584 B2
(45) Date of Patent: Apr. 6, 2010

(54) CAMERA BASED VIDEO GAMES AND RELATED METHODS FOR EXERCISE MOTIVATION

(76) Inventors: Timothy R. Pryor, 416 Old Tecumseh Road, Lakeshore, Ontario (CA) N8N 3S8; Marie C. Pryor, 416 Old Tecumseh Road, Lakeshore, Ontario (CA) N8N 3S8

( * ) Notice: Subject to any disclaimer, the term of this patent is extended or adjusted under 35 U.S.C. 154(b) by 0 days.

(21) Appl. No.: 11/980,717

(22) Filed: Oct. 31, 2007

(65) Prior Publication Data
US 2008/0125289 A1 May 29, 2008

Related U.S. Application Data

(63) Continuation of application No. 11/118,774, filed on May 2, 2005, now Pat. No. 7,328,119, which is a continuation-in-part of application No. 09/799,797, filed on Mar. 7, 2001, now abandoned.

(60) Provisional application No. 60/187,396, filed on Mar. 7, 2000, provisional application No. 60/187,397, filed on Mar. 7, 2000.

(51) Int. Cl.
G05B 11/01 (2006.01)
G05B 15/00 (2006.01)
A63B 71/00 (2006.01)

(52) U.S. Cl. .................. 700/17; 700/83; 482/8; 482/9

(58) Field of Classification Search .......... 700/17, 700/83; 482/8, 9
See application file for complete search history.

(56) References Cited

U.S. PATENT DOCUMENTS 5,772,522 A * 6/1998 Nesbit et al. ............... 473/222
2003/0108851 A1 * 6/2003 Posa .......................... 434/238

* cited by examiner

*Primary Examiner*—Ronald D Hartman, Jr.
(74) *Attorney, Agent, or Firm*—Stites & Harbison PLLC; Ross F. Hunt, Jr.; Douglas E. Jackson

(57) ABSTRACT

Disclosed are methods and apparatus for motivating persons to undertake exercise, employing camera based computer monitoring of persons and/or exercise apparatus, and displays of video data, which may be derived from such monitored information.

11 Claims, 12 Drawing Sheets

CAMERA BASED VIDEO GAMES AND RELATED METHODS FOR EXERCISE MOTIVATION

CROSS REFERENCE TO RELATED APPLICATIONS

This application is a continuation of application Ser. No. 11/118,774 filed on May 2, 2005, now U.S. Pat. No. 7,328,119 which is a continuation in part of application Ser. No. 09/799,797 filed on Mar. 7, 2001; now abandoned and which claims benefit of U.S. Provisional Applications, 60/187,396 filed on Mar. 7, 2000, by Tim Pryor, and 60/187,397 filed on Mar. 7, 2000, by Tim Pryor and Marie Pryor. The subject matters of which are all incorporated herein in their entirety by reference.

RELATIONSHIP TO OTHER APPLICATIONS

Touch TV and other Man Machine Interfaces (Ser. No. 09/435,854 which was a continuation of application Ser. No. 07/946,908, now U.S. Pat. No. 5,982,352);

Useful Man Machine interfaces and applications Ser. No. 09/138,339;

Ser. No. 09/789,538 entitled Programmable Tactile touch Screen Displays and Man machine Interfaces for Improved Vehicle Instrumentation and Telematics;

U.S. Ser. No. 10/611,814 filed Jul. 2, 2003; U.S. Ser. No. 09/789,538 entitled Programmable Tactile Touch Screen Displays and Man-Machine Interfaces for Improved Vehicle Instrumentation and Telematics;

PCT/US2004/09701 filed Mar. 31, 2004, entitled Reconfigurable Vehicle Instrument Panels;

U.S. Ser. No. 09/568,552 Picture Taking method and apparatus;

U.S. Ser. No. 09/612,225 entitled Camera Based Man Machine Interfaces;

U.S. Ser. No. 10/934,762 entitled Reconfigurable Control Displays for Games, Toys, and other applications filed Sep. 7, 2004;

Ser. No. 11/045,131 filed Jan. 31, 2005, entitled Reconfigurable Tactile Control Displays For Automobile Instrument Panels and other Applications; and U.S. Ser. No. 09/612,225 entitled Camera Based Man Machine Interfaces.

Copies of the disclosures of the above U.S. patents and co-pending patent applications are also incorporated herein by reference in their entirety. Additionally incorporated by reference are other patents and applications of Tim Pryor and his colleagues: U.S. Pat. Nos. 5,880,459, 5,877,491, 5,734,172 and 5,670,787

Also of reference are two articles, provided previously with the provisional applications: Consumer Reports, January 2000 issue, Page 15, and "3D human fashion model generation" by Textile Technology Co. (from the TC2 website).

FEDERALLY SPONSORED R AND D STATEMENT not applicable

MICROFICHE APPENDIX not applicable

FIELD OF THE INVENTION

The disclosed invention relates to methods for assisting and motivating persons with respect to various dietary and exercise regimens they might undertake, providing an interactive, iterative, "what-if" type of procedure where someone can see their predicted appearance in the future, also in clothes of their choice, and balance this with realistic expectations of what they may be able to achieve in terms of modification of their physical shape as a result of a planned course of action. The invention in a related manner also contains novel methods for helping persons with mental illnesses and other persons improve their quality of life and diagnose difficulties. In addition, the invention optionally links ones planned future appearance with the selection of clothing available for purchase today or in the future. This leads to new methods of clothing manufacture suited to such a strategy, and new and useful methods of purchasing dietary and medical items and apparel in the present and future, particularly from stores whose provided data bases accommodate the invention.

The invention also concerns an optional and unique life size display screen, a "digital mirror" so to speak, for input to, and display of, the computer aided models used, as well as inputs from a persons body sensed by TV cameras.

BACKGROUND OF THE INVENTION

The invention is concerned with predicting and displaying ones appearance in the future as a result of dietary and exercise programs, as a way to both chose a particular program and provide motivation for executing the program. It further comprehends motivation by showing what one would look like in particular clothes one might choose. There is no known reference predating our invention disclosing such methods or apparatus.

The invention in a related manner, also applies to the selection, purchase, and manufacture of clothes. Today, people buy "ready to wear" clothes by going into a store trying on a few examples, and hopefully, buying one—assuming their size is in stock, or the designs in stock are pleasing to them at a price they can afford. Of late, there has been identified a possibility of mass scale customization of clothes, using two (at least) technological breakthroughs—the fast programmable cutting of material in lot of one, and the ability of 3D measurement devices to scan a persons body at a large number of data points in order to give a custom data input to the computerized clothes design—in theory resulting in a perfect fit every time, and vastly reducing logistical complexity and cost related to stocking of multiple sizes and styles. (Consumer Reports, January 2000 issue, page 15, referenced above. See also as one example, the Proceedings of the 80th World Conference of the Textile Institute, April 2000 Manchester, U.K.). There is also a considerable body of patent art on various aspects of computerized clothing design, manufacture, and marketing, see for example U.S. Pat. Nos. 4,261,012 Maloomian; 4,546,434 Gioello; 4,916,634 Collins et al.; 5,163,006 Deziel; 5,163,007 Slilaty; 5,495,568 Beavin; 5,551,021 Harada et al.; 5,680,314 Patterson et al.

The basis of most 3D measurement devices is optical triangulation, for example as described in U.S. Pat. No. 5,362,970 or 5,670,787. Versions using scanning laser beams, and projected grids are most prevalent for the human body digitizing application which requires significant speed if done in real time, due to the problem of human movement.

U.S. Pat. No. 4,261,012 Maloomian, "System and method for composite display" seems to have been the first to associate an image of a customers head, with a stored figure image of a model. Subsequent inventors, such as Andrea Rose in U.S. Pat. No. 5,930,769, have refined the model, and worked out methods for interfacing with the manufacturing systems, and the way of doing business that surrounds the ability to provide clothing fit related fashion data to a consumer.

Recently some companies, such as Lands End, have introduced simplified data input means such that over the internet, one can look at a 2D image of what clothes you chose could look like on you. Lands End's effort is based apparently based at least in part on U.S. Pat. No. 5,930,769, the closest known reference to the fashion related aspects of the invention herein. In the Rose patent, the customer initially inputs information including body measurements and a digital photograph of the customer's face. Typical body measurements for women include; center front, arm length, bust, waist, hip, and height. Center front 2 is measured from the hollow of the neck of the customer to the navel. Body type/stature is also a desirable input to the Rose system.

SUMMARY OF THE INVENTION

Our invention discloses method and apparatus by which persons may visualize their appearance in the future based on actions they may take for themselves, in particular in undertaking a weight loss or exercise program also as a potential purchaser of clothing, the fit of which might also be predicated on successful execution of the program in question. The invention uniquely allows a "what if" scenario related to a display to the user of their future appearance, under the influence of variables affecting same, primarily diet, and exercise. This in turn allows one to evaluate the various tradeoffs and to optimally select a program, modifying it along the way and modifying expectations as needed.

Method and apparatus are disclosed for improving the likelihood of success of a given health plan by prediction of future appearance and providing an ability to monitor the movement and shape of the user in order to tailor the plan, and the video or other instructions and stimuli given the user to suit the situation. Direct feedback to the program and back to the user from remotely located internet sources or local DVD or other data storage is enabled as desired by the novel inputs, many of which have been disclosed in co-pending referenced applications.

The foregoing capability of the invention is believed to provide a high degree of motivation for maintaining a regimen for weight loss (or less commonly, weight gain), or other physical modification activities. It is thus important as at least a partial answer to the "obesity crisis". This application also explores some other aspects of this relating to improved prediction of physical shape in the future by tracking progress via measurements taken as a function of various diet and exercise, and the continual feedback of this updated model to both the customer, the trainer or dietician, and to the manufacturer where apropos. In addition the invention provides incentives to stick to a diet and exercise, by giving not only fashion or other appearance related inspiration, but by tailoring workout videos and the like to suit the persons needs, such that the workout may be paced to the actual action and needs of the person and in conjunction with a chosen dietary and exercise or other health plan.

Hardware and software systems incorporating automatic and semiautomatic measurement are disclosed useful for stores and "Weight Watcher" type meeting rooms, as well as the home. Further Improvements in merchandising and manufacture of garments are also disclosed which relate to the ability to predict future needs and shapes of customers.

In the sense of clothing selection, neither Rose, nor any other reference has addressed the "what if" future scenario possibility—that is, "what will I look like in a particular outfit, if I take some action"? And what are the tradeoffs between selection of apparel and the achieving a new figure, in a given time period?

Nor has anyone addressed the issue of "what will I look like in a particular existing outfit or design, if I, or the manufacturer, or an intermediate party, do something to it"? And what are the tradeoffs between selection of apparel and alteration, in a given time period and at a given cost? In addition, none heretofore appear to have addressed the hardware and related aspects that would make the shopping experience using the technology available, really useful and effective—especially in a home environment.

The invention also allows one to model a business as to how this affects clothes choice and ramifications thereof, including into the future. It provides a method to visualize oneself full size—with respect to attire, hair, accessories, and many other things making up ones impression on the world, also including the effects of diet, exercise etc on ones future appearance. Indeed using the invention, and with the advent of affordable large screen displays, the digital model created can be displayed "life size" even in a persons home, just like looking in a mirror in a clothing store (or at home), but instead seeing a "Digital You", in a particular outfit, and with the benefit of an exercise or weight loss or gain program, or other means to modify your appearance if desired (including in the final analysis, the choice or dimension of prospective clothing itself). Because it is a simulation, one can "try out" not only different clothes in a lifelike way, but also see the effects on your appearance in one article or another, in one size or another or of different weight loss regimens over different time periods for example.

Given all of the advantages, it is thus a goal of the invention to provide method and apparatus to allow one to visualize, create, and modify a model of oneself or others in clothes of interest, and to do so in a manner convenient for a large number of users.

It is a goal of the invention one to predict and display the effect on ones appearance (clothed, or even unclothed) of future activity chosen, such as diet or exercise, also as a function of the apparel chosen. And it is a goal to allow one to iterate the prediction, such that a one can optimally tradeoff the various factors such as caloric intake, exercise time and the like, with ones appearance predicted to result from doing same.

It is a further goal to provide one an incentive to first choose, and then to stick to a diet and exercise plan, (including modifying it as need be), by giving not only fashion or other appearance related inspiration, but by tailoring workout videos and the like to suit the persons needs, such that the workout may be paced to the actual action and needs of the person if desired.

It is an added goal of the invention to improve health and self-confidence by motivating persons to stick to a dietary and/or exercise plan and to optionally provide a means for dynamic model animation by which one can visualize the way in which ones body changes with regimen selected It is a goal of the invention to provide interactive choice of dietary and/or exercise plan regimen to maximize an attainable result desired, and to provide predictions of ones measurements or shape at a certain point in time, if a plan is undertaken, which plan can be constantly up dated to either arrive at the same shape, or a new shape.

It is a further goal of the invention to provide a simple means for entering 3D data points from a persons body into a computer program to graphically model their body or a future manifestation thereof in 3 dimensions.

It is a goal of the invention is to provide data dynamically during exercise, to see the effects on ones appearance of continuing a given regimen, or changing plans. It is an additional goal of the invention to provide methods to assist in the treatment of mental, behavioral, or other disorders, and in situations where a form of companionship may be provided the user.

It is a further goal of the invention to provide an improved method for selection and purchase of clothes, including the purchase of clothes in the future. And it is a still further goal of the invention to provide an improved method for the manufacture and distribution of clothes, lowering the price thereof, also by providing a method for prediction of future clothing needs and production planning related thereto and model a business as to how this affects the clothes choice and ramifications thereof in the future, and to produce or inventory garments in new ways not heretofore economic.

These and other goals of the invention are illustrated in the following figures:

BRIEF DESCRIPTION OF THE DRAWINGS

FIGS. 2a-2e illustrate several methods and apparatus how the invention may be utilized to provide input data, to react with a number of interactive clothes choices and diet/exercise regimens, which addresses weight, figure, or clothes choice related dimensional input issues to the digital figure model. Illustrated are systems ideal for use In home or Boutique, which can include modifying dimensions looking at digital model and moving your hands, touching a screen or the like.

DESCRIPTION OF THE PREFERRED EMBODIMENTS

FIG. 1

A discussion of 3D digital models of humans and dense scan data methods of creating them is given by Textile Technology on their web site, referenced above. These models can be created and changed by their method, by means herein disclosed (as well as in co-pending references), or other methods. A real benefit of the means herein disclosed is that the equipment is simple, and can be used in the privacy of ones home. It is ideal for updating of complex models once created. This is particularly of use, as by definition ones figure changes with diet and exercise, and the "present" model then can be, and should be, changed to suit. Its noted that one can store models, so that the "before" "present" and "future goal" models can all be compared. This is a sophisticated way of picturing results, far beyond the common practice today of comparing scale readings.

There are several models of interest in this application. One is the basic human Body Model, such as shown in referenced articles however, initially created. A second model is what is here called the Dressed Model, that is the basic model with the clothes fitted to it, using a best fit routine or some other fitting procedure applicable to the type of clothes in question. For example, if pants are to be fitted, a first step could be to fit the pants model to the basic human body model at the waist, and provide this view to the customer. The view could also be provided with the pants slipped down an inch as well, as often happens when pockets are full, or while walking etc. This is one of the benefits of simulations of this type—a whole range of characteristic situations can be tried very quickly to see their effect, in this case perhaps convincing the customer or seller or modifier to make the pants cuffs a bit shorter.

Figure 5:
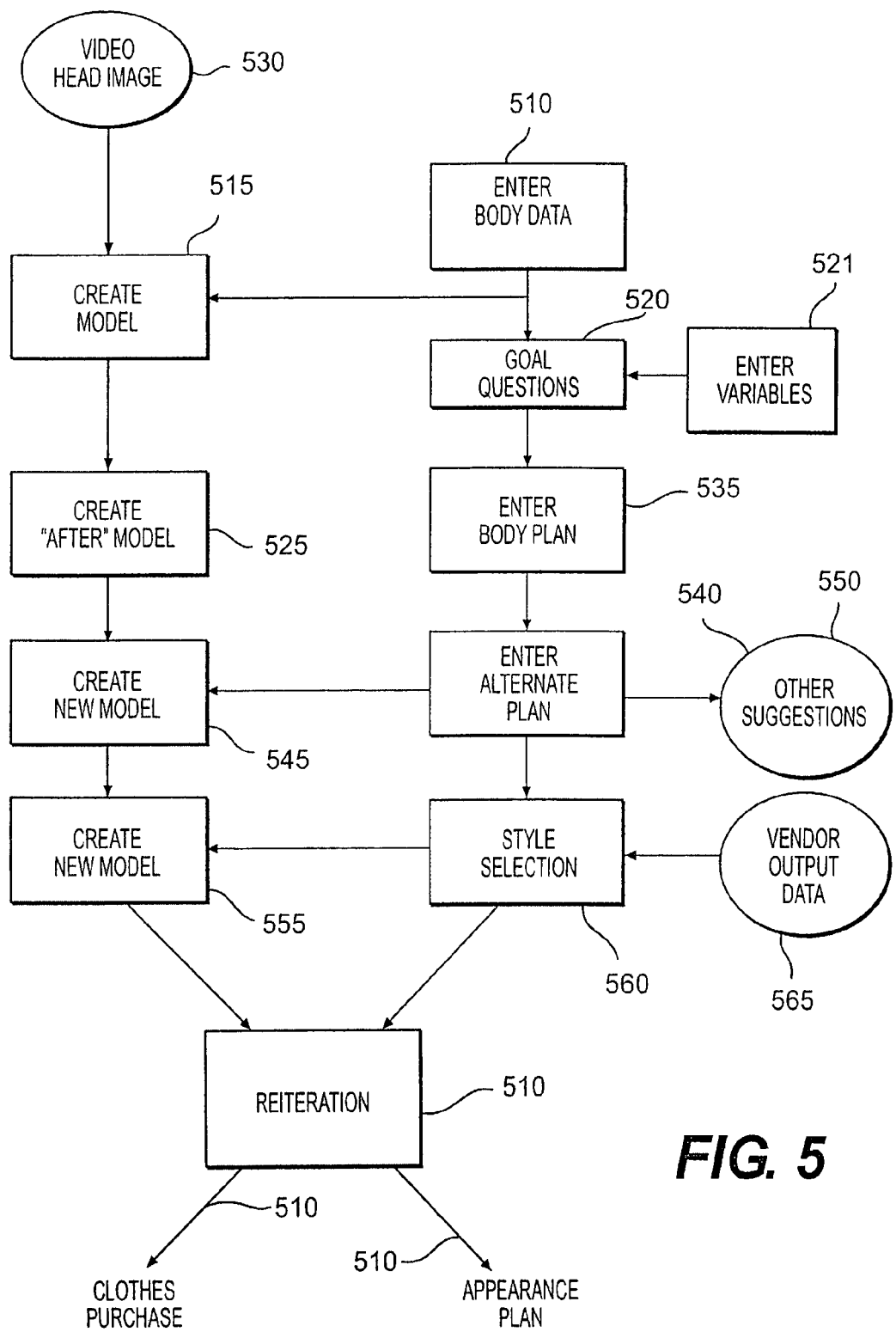
FIG. 5 illustrates methods which address weight related dimensional input issues to the digital figure model and how the invention may be utilized to provide data as to ones future appearance.

A further model, discussed in FIG. 5, comprehends a future Body Model, with its attendant Dressed models as disclosed herein.

For this application, the display used for the digital model presentation is preferably located in ones home and is preferably a life size display, today created by a projection type system, typically rear projection. The digital image produced is not only created but then modified using an ability to touch ones self or ones digital self (and potentially projected future self) represented on the screen. With the advent of affordable large screen displays, especially those on the horizon for HDTV using low cost micro display based projector systems, the digital model created can thus be displayed "life size" even in a persons home, just like looking in a mirror in a clothing store, but instead seeing a "digital You", in a particular outfit, and with the benefit of an exercise or weight loss or gain program, or other means to modify your appearance. Because it is all a simulation, one can "try out" not only different clothes in a lifelike way, but also see the effects on your appearance in one article or another, in one size or another, and in one state of alteration or another, for example.

Figure 1:
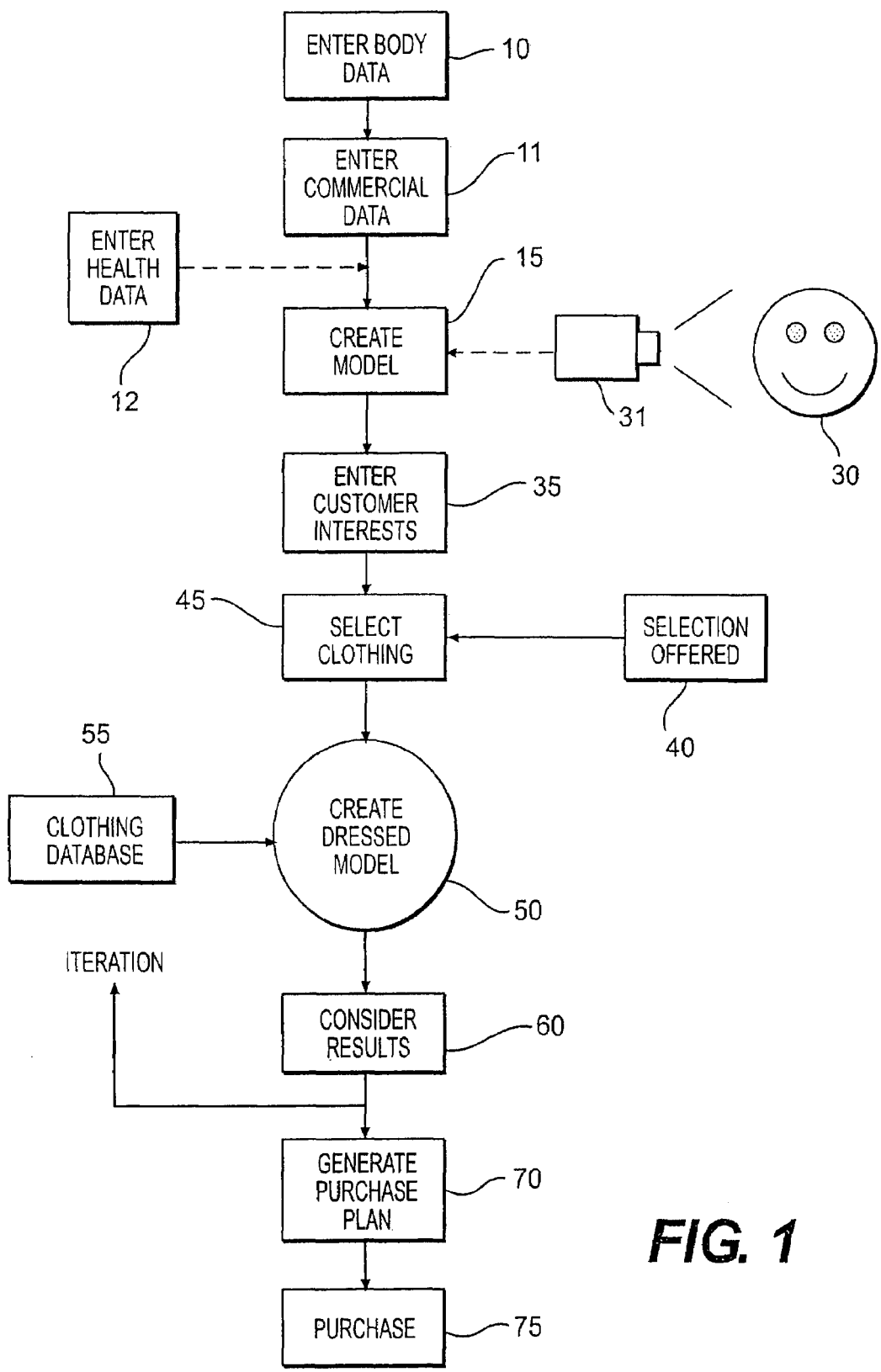
FIG. 1 is a Block Diagram of how the basic invention is utilized to provide input data to ones digital model, and to utilize data there from, also as to ones future appearance and in consideration of a number of interactive clothes choices and diet/exercise regimens.

FIG. 1 is a Block Diagram of how the basic invention is utilized to provide data as to ones appearance in clothes of a given type. This can be used solely for the purpose of prediction of ones appearance, in a given set of clothes already on hand, or in an interactive "what if" tradeoff analysis, with a selection of clothes to be considered for purchase, with various types and costs of alteration strategies, or partial custom assembly strategies, including select fitting of components and/or custom tailoring of one or more components, and/or alteration of one or more already made components.

In general for this purpose, the body may be measured, not just for its dimensions that relate to fit of clothes per se (for example the basic ones in the Rose patent), but also with respect to certain dimensions and other medical factors if desired that define ones shape. Height, weight, age, general stature, and other factors—including any special case issues, may also be inputted as well.

The invention contemplates that the actual procedure can vary. A typical embodiment would do the following. First in step 10, the user enters their dimensions and other information as called for by the program, which may include, for example dimensions of key parameters of the persons body necessary for establishment of a minimum 3D Body Model. For example, some are mentioned above per the Rose patent, including waist size, arm length, neck size, shoulder dimensions, etc. Generally one would also enter ones current size as you understand it for what ever the garment item is, giving the program a place to start and the ability to cross check for the rationality of the dimensional body data inputted (with suitable questions presented to the user if the two did not reasonably match). It is contemplated that increasing levels of model sophistication will require many more dimensions as input.

In addition the user may add in step 11, any commercially relevant data, for example desired delivery and cost data, and whether or not one wishes to consider alteration strategies and the like. Optionally, in step 12, Physical body health related dimensions and other applicable parameters such as % fat mass, stature, etc. These are needed if prediction of the future model shape is desired (discussed further in FIG. 5), and may include other physical health related data, including Medical history as applicable.

This data is then provided to the program, which generally is located distant and accessed over the internet, but could alternatively be on DVD disc, CD Rom or other local storage medium, or downloaded thereto off the internet for example. A model 15 is then created of the person today. The model can be a 3D digital model created by known means, for example using a 3D solid model package such as "CADKEY". Such a model is shown in the referenced Textile Technology article.

It is contemplated that the entry of data can in some cases be automatic using for example, features of the invention, or the inventions disclosed in the co-pending references.

The program in the second step then optionally can ask one or more questions, for example questions related to the degree of fit desired, for example tight fit, loose fit, baggy, etc. it can even be specific as to where—in the buttocks, for example. It can also ask if one wants to fit a certain size, or and if one doesn't, what it would take to do so with various suggestions made by the program to do so, such as methods to lose weight for example (see also reference 8).

A Body model 15, of the person is created from the measurements, and a video image of the users head 30, taken for example using camcorder or TV camera 31, superposed if desired, as in simply done in the U.S. Pat. No. 4,261,012 patent (Maloomian), or with more views taken as is desirable and taught by Rose. The model at this point more or less looks like the person.

The customer then tells the program what they are interested in 35, and picks the specific clothing 45 they are interested in from the selection 40 offered by the vendor program, or suggested by same given taste data entered by the customer. This step can include several iterative consultation steps with the program or a real consultant on line. The clothes selection step could involve an automated, or even human on line fashion consultant as contemplated by Rose.

The dressed model 50 of the person, is then created (typically on a remotely located program at the clothing vendor site) using a Clothing data base 55 typically at the vendor site of the clothing itself and the results (and perhaps the whole data file) presented, typically as a display on the dressed model, to the user in the clothing selected by the user from styles and sizes presented to same by the program, given the users taste. Such data 55 would typically, but not necessarily be provided by the clothes vendor, for example on their web site. Alternatively the clothes data base could be downloaded to the user, and the fitting done to the model locally at the user site using stored programs there. Areas which need attention fit-wise, if any, are then highlighted by the program, and or inputted by the user as disclosed herein.

The user in step 60 can now consider the results and decide what to do. Most typically, the user would iteratively repeat the steps described above, also with the input of different clothes styles and sizes, together with continual iteration of diet and exercise plan,(if considered, as discussed below), until the desired practical appearance and clothes purchase (possibly for future delivery) plan 70 is arrived at. Since the invention contemplates method and apparatus to do all of this in private, there is no embarrassment, and a realizable plan can be achieved.

Such iterations could be lengthy, and the subject of debate with the users peers, family members, health advisors, weight watcher groups, and the like. And it could go on for several days or longer—impossible in a store or other public venue under most conditions. A final, "purchase" step is indicated at 75.

FIG. 2

For someone wishing to buy clothes over the internet or other home shopping venues, we feel it is much more convenient to provide measurements taken in your own home. This, in the Rose patent, requires you to manually take the measurements yourself and type them in, not too difficult if only a few are required, but still prone for error and for many, unattractive. In general, it would be more desirable to have some or all of the measurements automated and to be able to take many more—which then could lead up to the mass customization of clothing in lot of one discussed in many textile institute papers. And for those interested in predicting their future appearance in clothes of whatever style and size is of interest to them, they must input their present shape, their intentions, and possibly other medically related data. This is data that most people want to keep private. An overweight person for example, may be uncomfortable going to some emporium where measurements are taken.

In addition, many people are uncomfortable in shops, letting others measure them and suggest sizes or alterations, particularly if the result suggested exceeds a preconceived idea of the customer of what they should be (but not necessarily are). Many a sale has been lost this way, or many a person has purchased a size too small, just because of a lack of candor in this regard. The invention solves these problems, because tasks normally done in a store are enabled in the home (though the invention can be used in stores as well).

FIG. 2 illustrates several embodiments which answer many of the dimensional input requirements. Many features are also discussed in co-pending applications incorporated by reference.

As pointed out, ones basic body dimensions can be inputted manually, as in the Rose invention, or inputted from a full 3D scan such as disclosed in the referenced articles (which today would need to be done in a special facility, but which could be done at low cost in the home using the invention, if suitable software and training were provided, for example over the internet from a remote source).

Regardless of how data was initially inputted, it would still be desirable to periodically, and if possible, automatically, update the model of the person, especially during a period of weight change or exercise. And it is useful to provide data on existing clothes from ones home, to interact with designers of future clothes or those providing alterations to existing clothes. This can be the case where you tell a remote source of clothes, that you want something just like a garment you have but with the following differences . . . (size, color, pleats, lengths, pattern, ad infinitum).

For automatic entry of dimensional points on the body or clothing, several types of sensors are possible. Illustrated particularly here is one class, that of electro-optical and particularly TV camera based sensors. These sensors are inexpensive, accurate, have large range, and in many cases are able to acquire multiple data points on the person at once. In addition they generally are digital and largely drift free—important for calibration purposes, and measurements taken over time as in during months of dieting for example. Four camera based sensor versions are here shown, all which use Single or Plural TV cameras to obtain data at low cost in the home or wherever. For use with a plurality of cameras such as stereo camera pairs or triplets, these are:

Use of a laser spot pointer;
Use of a touch finger, or finger pair (also thumb and finger);
Use of a laser line pointer; and For use with the above stereo cameras, or even a single camera, a mechanical probe with multiple target datum's.

In general, there are two modes for such application which are "Natural" in the sense of one being able to perform operations similar to those learned in everyday life. In the first case, you can stand back, and look at a digital display of yourself in a "mirror" (in effect a digital display, preferably full size, such as a Rear Projection display) and touch (or otherwise indicate on) ones self where action is needed, which is sensed and via a computer program causes digital model to be modified. The modifications undertaken are either to the base model of you with no clothes, or more specifically the case in this application, the Dressed Model, with clothes on you, as if you are showing a tailor or even a designer what to do. For the future weight/shape aspect, this could be showing a weight loss trainer or health professional, for this aspect of the invention indicating you wish to lose mass in a certain place.

In the second case, you can look at your digital image in the "mirror" (that is displaying the image of the dressed digital model of you, and reach out and touch the image (as opposed to yourself, in the case "A" above). Your finger position is sensed, which communicates to the computer and thence to the dressed digital model what point on the model to change, and as you move your finger, the degree and direction of change can be registered. It is noted that using a new LCD based video mirror "Miravision" product from Philips, the display can actually change under electronic control into a real mirror and back again. This allows it to be a historic life size mirror, when not used as disclosed herein.

Figure 2A:
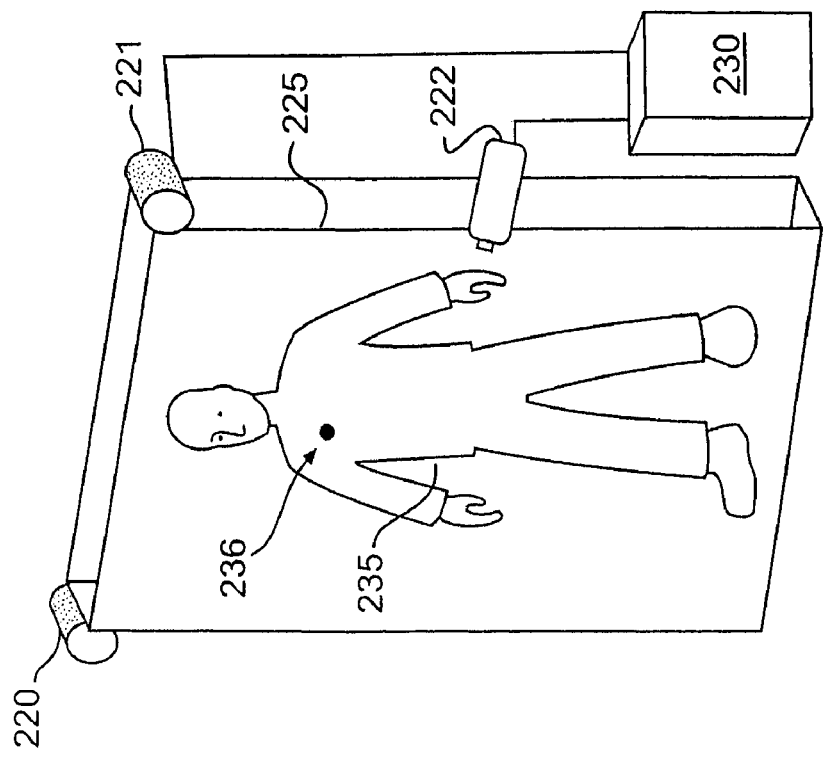
Figure 2A:
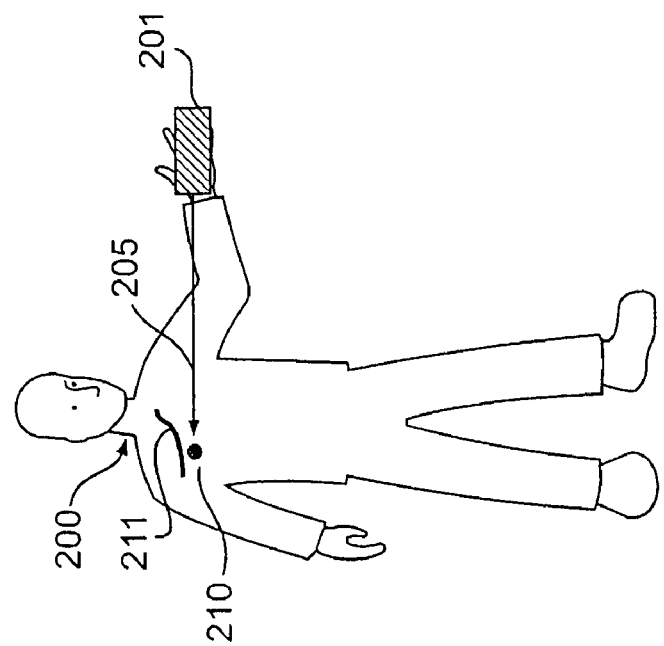
Figure 2B:
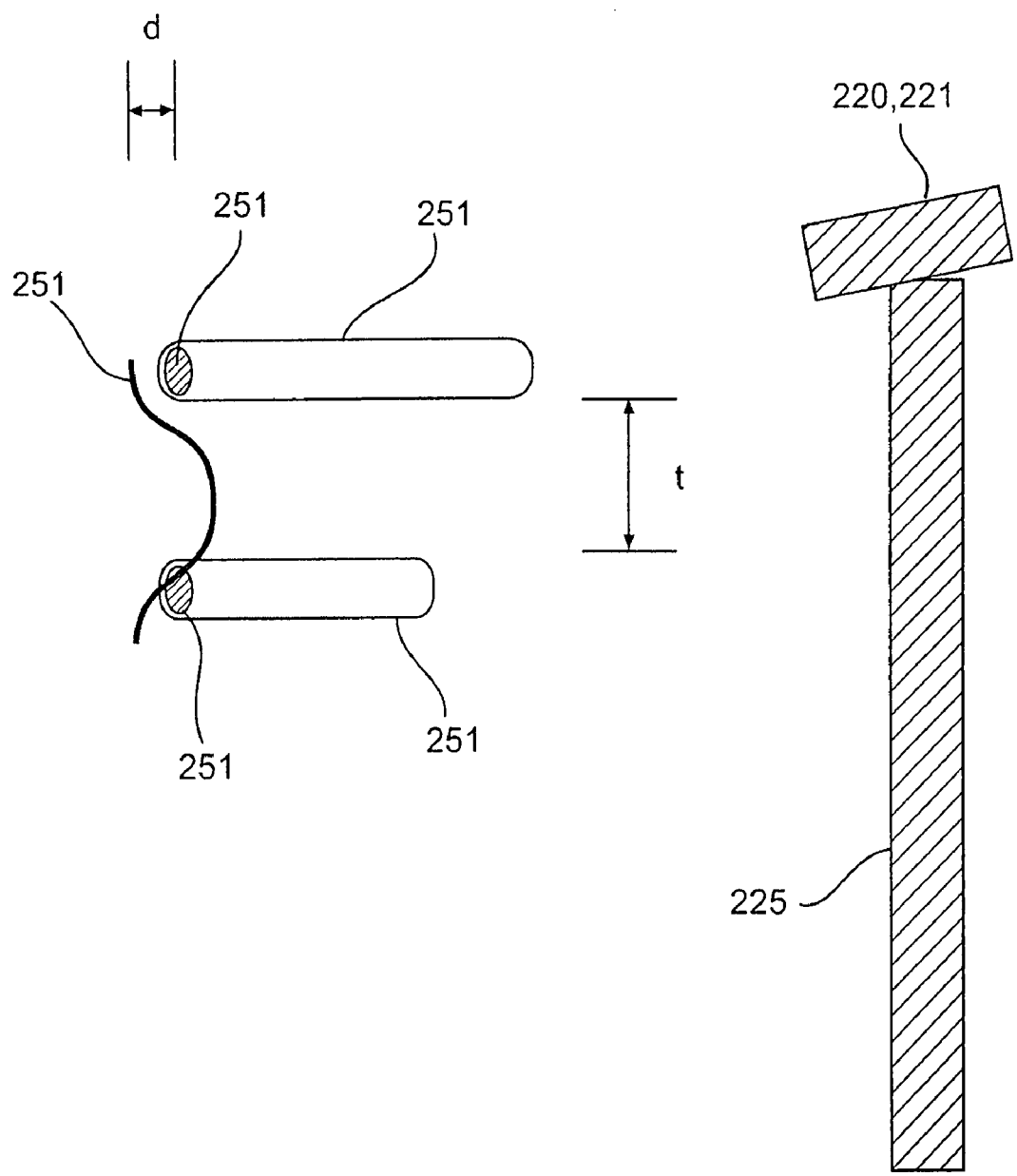
Figure 2C:
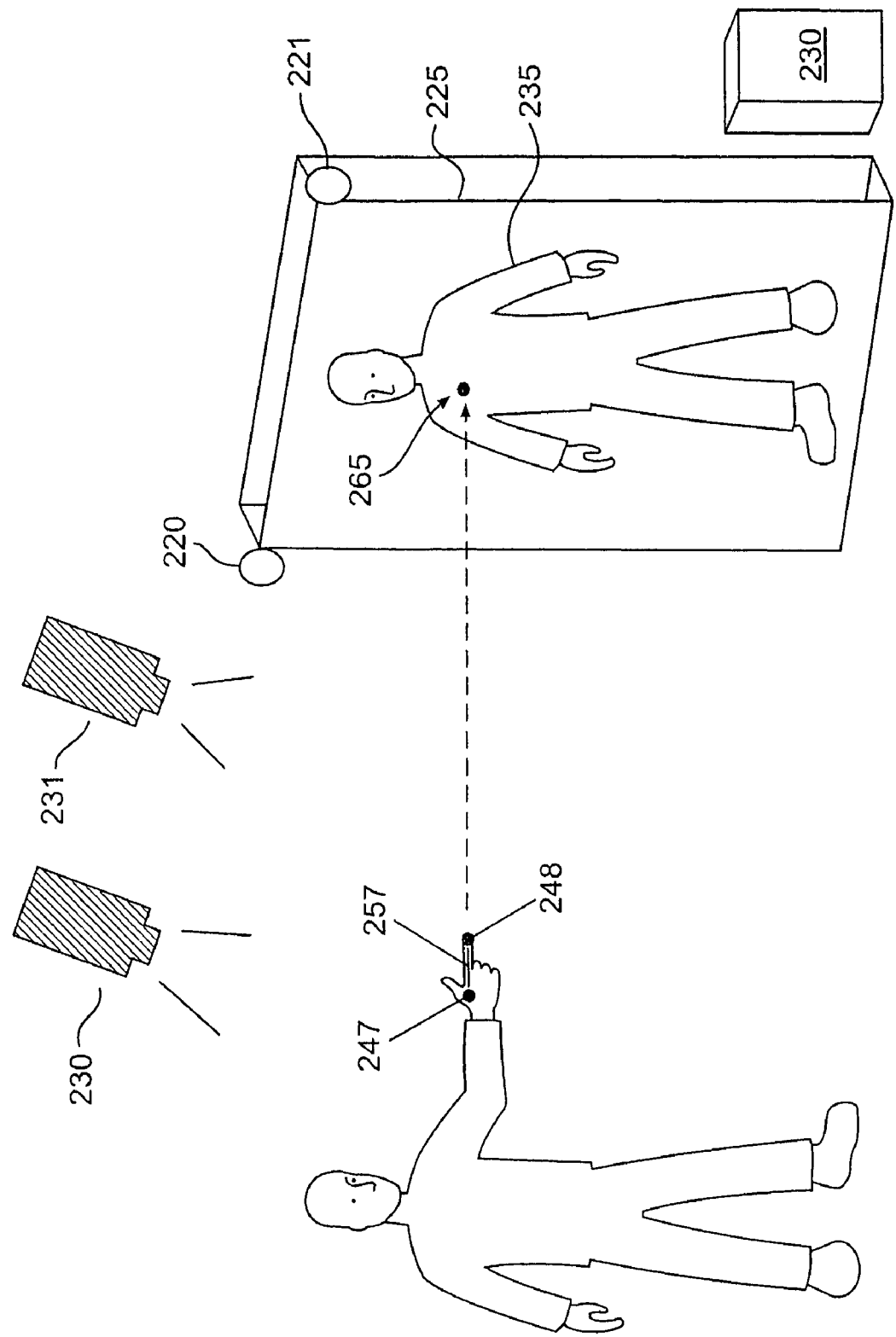
Figure 2D:
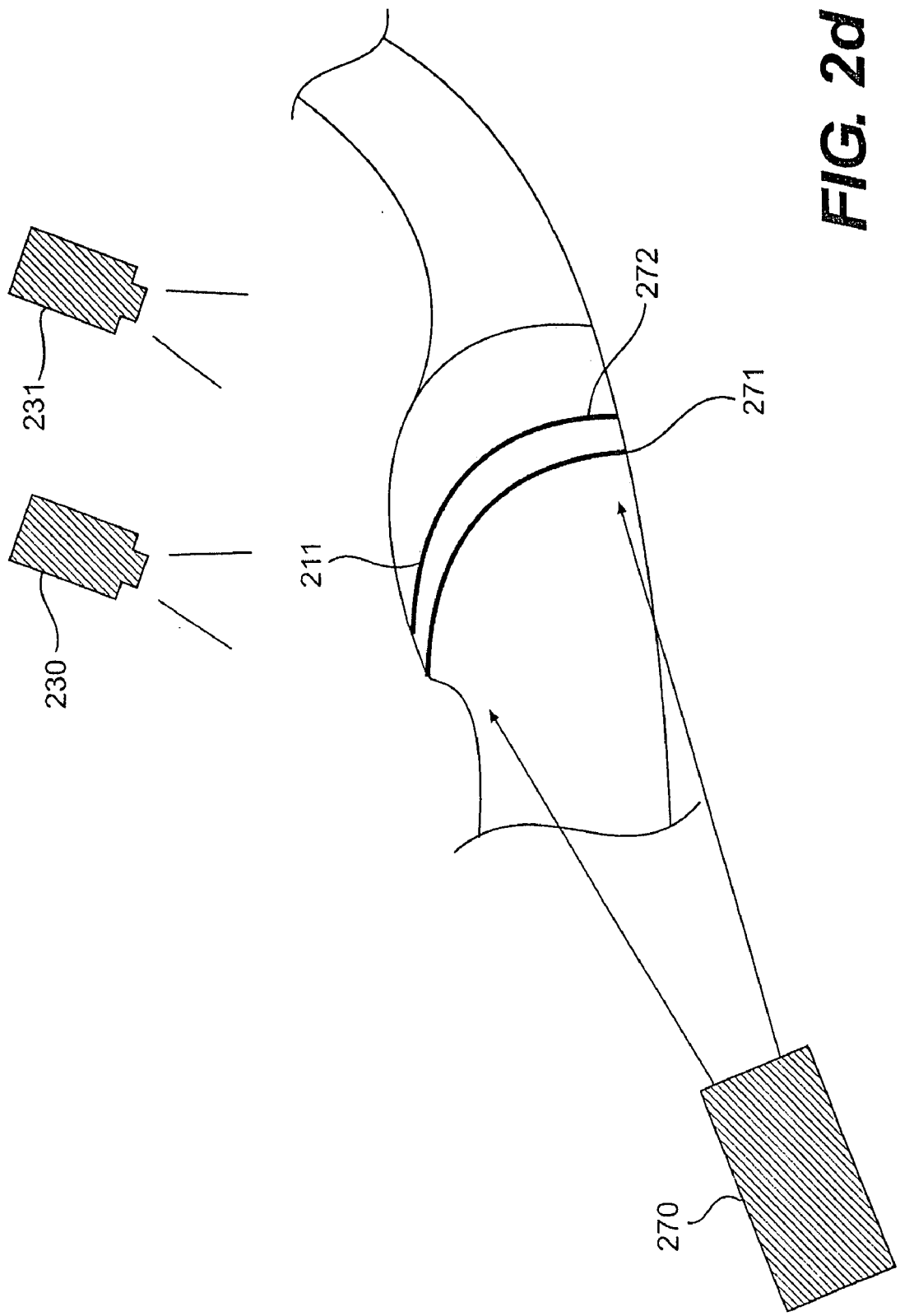
Figure 2E:
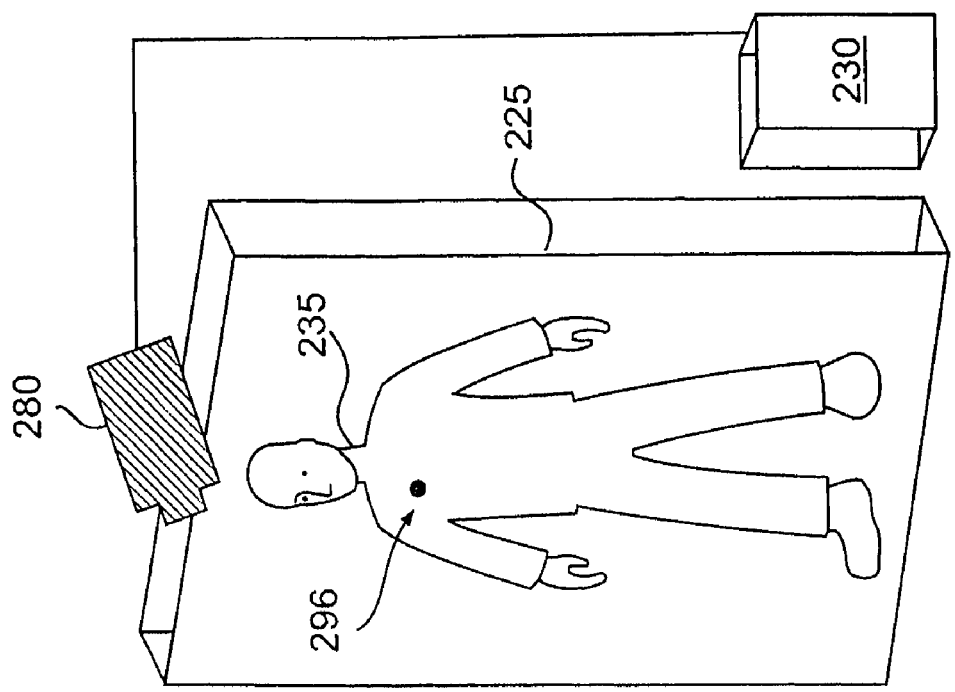
Figure 2E:
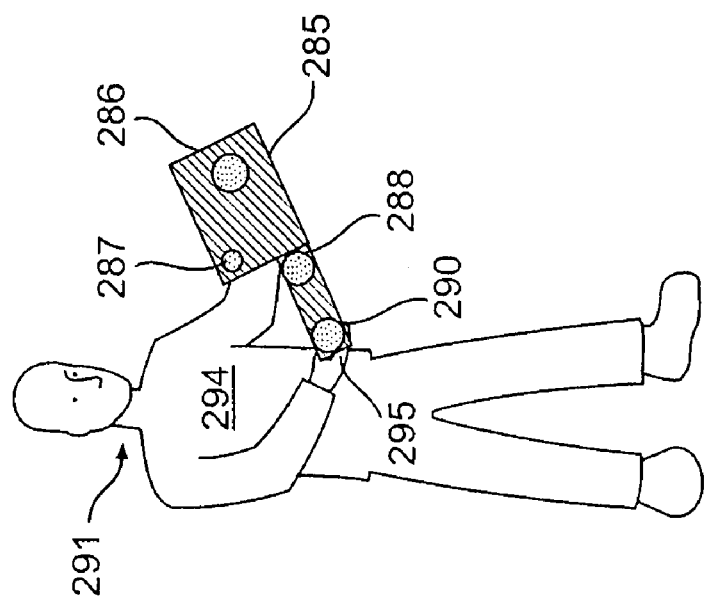
Figure 3:
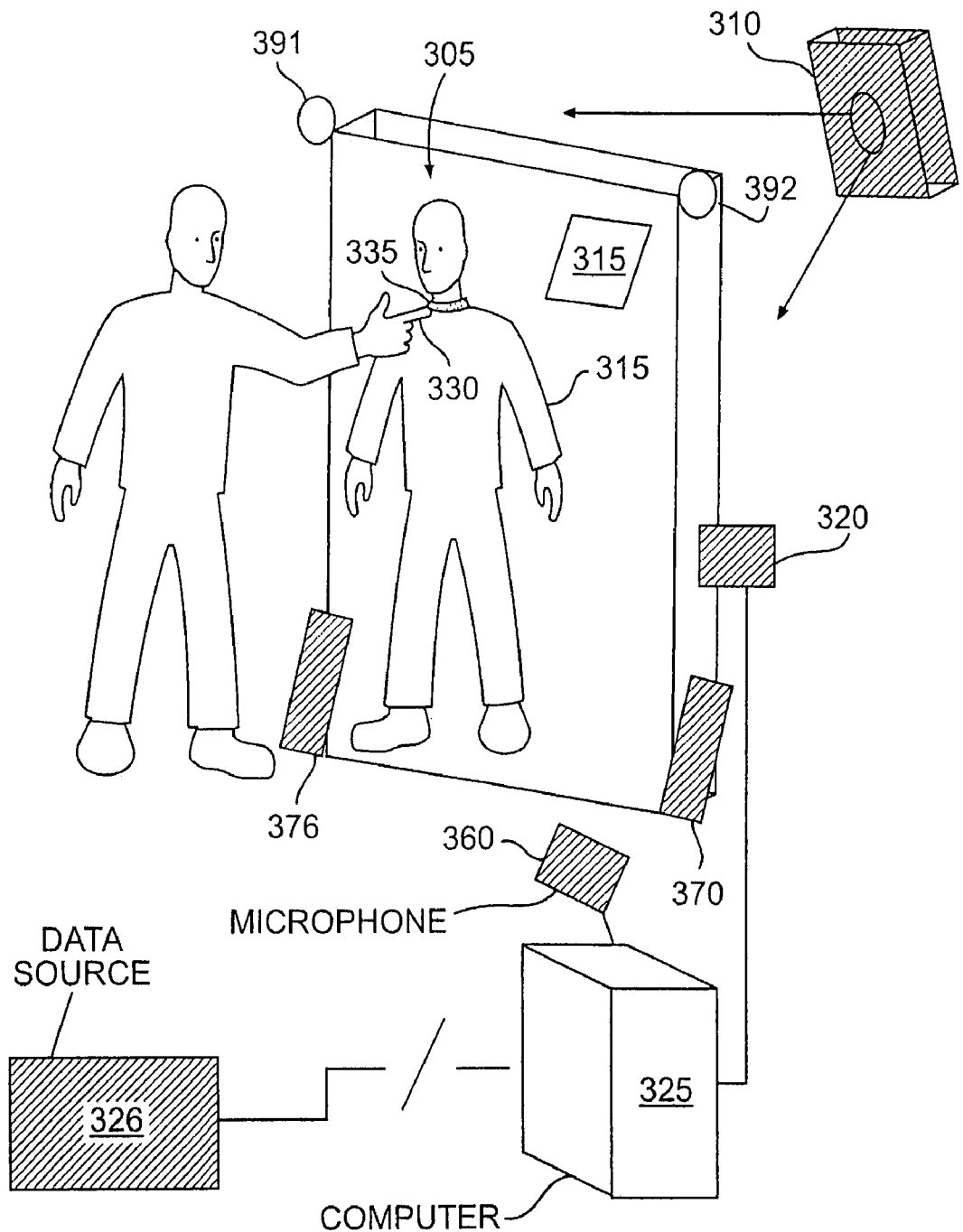
FIG. 3 further illustrates data input and display using the invention, particularly with a touch screen, also illustrating logistical and commercial aspects of the invention, display in ones home or elsewhere is preferably life size screen, and the digital image produced may be created or modified using an ability to touch (or otherwise indicate on) ones self or ones digital self (and future self) represented on the screen. An interactive session of a user employing the inventions method of inputting and providing dynamically variable choices of alterations or styles, or even entire lines of garments is disclosed.

In FIG. 2 your finger or another object or data point, is directly sensed by cameras, while in FIG. 3, the point of touch on the digital model representation is sensed (for example using a touch screen, although the fingers could be sensed alternatively). In the latter instance, you can look at your digital image in the "mirror" and reach out and touch it, with your finger position sensed, which communicates to the digital model what point on the model to change. Since the screen is two dimensional, the touching is not quite correct in a 3D sense, but can be made more realistic through the use of stereoscopic displays with 3D glasses and other 3D display technologies if desired.

FIG. 2a illustrates use of a laser pointer (or other optical designation device), by which a person may designate spots on a person or clothing which are digitized in their position by cameras of the invention, including as desired other features in the vicinity of the identified spots. The pointer is held by either the user, or another person aiding the user. Or it can be fixed, with the user moving his or her body to intersect the spot. As has been discussed in co pending referenced applications, the laser spot location can be digitized in 3D if the laser pointer to camera angular relationship is known (easiest if both are fixed, see for example U.S. Pat. No. 5,362,970), or if a stereo pair of cameras are used, whose relation ship is calibrated or known. For added information on use of single camera or two camera stereo techniques see for example, A paper by Dr. H. F. L. Pinkney entitled Theory and Development of an on line 30 Hz video photogrammetry system for real-time 3 dimensional control presented at the Symposium of Commission V Photogrammetry for Industry, Stockholm, August 1978, together with many of the references referred to therein gives many of the underlying equations of solution of photogrammetry particularly with a single camera. Another reference relating to use of two or more cameras, is Development of Stereo Vision for Industrial Inspection, Dr. S. F. El-Hakim, Proceedings of the Instrument Society of America (ISA) Symposium, Calgary Alta, Apr. 3-5, 1989. This paper too has several references to the photogrammetry art).

As shown, person 200 holds laser pointer 201, and aims it at their chest area 205, the spot 210 on the unwanted crease 211, is detected using stereo TV camera pair 220 and 221 which in this case are located on the corners of display screen 225. Both the display and the cameras are controlled by computer 230. See U.S. Pat. No. 5,362,970 for information on how to reliably find the spot location in the camera field. Alternatively you or a friend may aim a laser pointer at a TV screen display of the virtual image of you "in the mirror", and the point of impact is sensed on the virtual image and read into the computer.

While triangulation using a single camera and a known laser projection direction with respect to the camera optical axis can be used (as discussed also in U.S. Pat. No. 5,362,970), this does not allow the generally desirable freedom of pointing possible when two cameras such as herein disclosed are used (whose fixed angular and positional base line allows determination of spot location no matter from what direction the spot is generated).

The camera images produce a stereo pair which is matched in the computer and using real-time photogrammetry, the location of spot 210 in x, y & z is determined using known techniques. This spot is then used to identify to the computer that crease data is of interest, for example in the dressed digital model 235 projected on the screen 225 under control of computer 230 connected to the projection device such as a Sharp Brand LCD based projector (not shown). The fact that the user pointed the spot at the crease on the chest could be announced to the computer by voice or other means as well. (acts also as a double check on the sensed spot data).

It is noted that the crease 211 might be on the dressed digital model rather than on the person, and in this case, the laser spot 210 could be pointed at the model on the display screen, with its indication on the screen determined as shown in FIG. 2B below relative to the alternate tack of pointing at the feature of interest in the model image on the display screen.

The point 236 on the digital model, corresponding to the inputted data of desired location on the human, in this case the point hit by laser spot 210, can also optionally be displayed for reference. This is useful, for example, in modifying the point touched, or in supplying corrections to the model.

Alternatively, the laser spot can be used to determine the persons size or shape. In this case, the user sequentially can point to a succession of spots, for example in a bicep or midriff area, whose position is digitized and a sectional shape or 3D volumetric image of the area in question built up. This can be used to create a more accurate model, (assuming for example, that one started with a standard model of a person of a given height and weight) or can be used to update a model, for example created initially with specialized triangulation based scanning equipment as described in the referenced articles. See also FIG. 2c. Additional cameras such as 222 can be added to improve the stereo photogrammetry solution used to find the spot position or other data. Note that the spot can also be used by the user to identify to the computer system connected to the TV camera (or cameras)some other feature such as an edge of material such as a pants cuff or some portion of the body, whose edge position is desired to be determined by camera image analysis using known machine vision software (such as VisionBloks from Integral Vision division of Medar Inc) located in the computer. For example, if the laser spot projected on ones chest, might be purposely done so to identify a button resident there to the computer and camera system for input to a local or remote data base. This button, once identified, would be scanned by the camera system and using such image processing software its data would be inputted to the data base. For example, if the laser spot on the arm might be used to identify to the cameras the location of the persons elbow in 3D space.

FIG. 2b illustrates the use of a woman's fingers to pinch excess cloth in the breast area of a garment she sees on a virtual display, with a stereo pair of cameras as shown in FIG. 2A to resolve the x, y, and z locations of the finger tips vis a vis the camera system, and optionally a large screen display, preferably full size (discussed further in FIG. 3 next). In a referenced co-pending application Ser. No. 09/138,339, a similar application for clothes design was noted with the model pinching or touching the actual cloth on herself, to indicate to a designer (who might be remotely located) and area which needed attention. In either case the data as to the problem is inputted to the computer system, also optionally using in many cases voice commands, such as "take it up", "too tight", "too loose", "too bunched up", "smooth it out", etc. Alternatively, the same technique for can be used to measurement of fat on the body itself, for example at the waist (or elsewhere for input into weight reduction programs for example.

In this case at least two sensing modes are possible. First, the positions of a persons fingers can be directly sensed by the cameras. However this has some problems in the amount of image processing needed to find the tips of the fingers in a reliable manner using affordable image processing computing which doesn't take too long for user comfort. To aid in this the illustration of FIG. 2b illustrates a situation (exaggerated in size for clarity) where the user has on his finger and thumb artificial targets (much as one would put a thimble on today), which could be LED's or retro reflectors, or other clearly distinguishable datum's including contrasting or even retro reflective nail polish, or patterns on material as another example.

Consider FIG. 2b where the case of LED targets 245 and 246 (powered using batteries or a power supply connected by wires not shown for clarity) are located on the thumb and forefinger 250 and 251 of a user. The LED's are in the simplest case, sequentially illuminated and the stereo camera pair 220 and 221 determine their locations on sequential TV frames. If one is pulling a fold 255 outward a distance "d" at ones waist, this distance d can be determined by comparison of the locations in 3D space of the LED's (or in a 2D view if the user is facing the cameras in an aligned manner). Clearly any location or difference in locations on the body or clothes on the body can be so measured, and such used as inputs to the Body or Dressed model as appropriate. Note that for clarity only a part of the human user has been shown.

If instead one is pinching the fat 255 of thickness "t" at ones waist, as opposed to a fold of material 255 in the instance just mentioned, this thickness t can be determined by comparison of the locations in 3D space of the LED's (or in a 2D view if the user is facing the cameras in an aligned manner). Such fat thickness data is often an input to diet and exercise programs, and clearly any location on the body can be so measured.

In some cases it is desirable to locate the stereo camera pair in other locations or to provide added cameras, such as overhead cameras 230 and 231 (dotted lines). Generally it is useful for the cameras to be located on or near the screen, as is often desirable for mounting and packaging purposes Another use of the cameras is to determine pointing direction, so that a user can point at something on is displayed image that he wants to modify or create or whatever. For example, a line target viewable by the cameras such as retro-reflective line 257 or a pair of targets such as 247 and 248 can be used on the forefinger, to allow the pointing direction of the forefinger to be determined. In this manner, the finger can point at the displayed image on the screen, and the zone of the image pointed at, such as point 265, determined, and displayed on the model by using the computer to feed a point generation command to the display driving electronics. A detected point such as 248 on a forefinger can also be used for other purposes, for example to point at an region of interest, or to trace around an contour of interest, such as ones thigh to aid the modeling of it, or whatever. The point is tracked by the cameras and a sequence of data points assembled in the computer to create a contour of the region or a thickness determination thereof.

FIG. 2d illustrates use of a laser line or grid pointer to provide structured light sectional data when observed with a stereo pair of cameras whose dimensions are known such that the line sectional data can be digitized. The movement of a spot around a surface to sequentially digitize the surface coordinates is time consuming, and runs the risk that the person moves between points. It is generally better for this purpose to use a line type source such as laser line pointer 270 (comprised typically of a diode laser whose beam is expanded in one axis by a cylinder lens) producing where a whole line 271 of points on, in this case ones arm bicep 211 shown in close up. The stereo camera pair 230 and 231 with suitable image processing to extract the line image and photogrammetry to compute location of all the points on the line (in almost all cases of angular orientation of the line to the cameras, and if three or more cameras are used, in virtually all cases), giving the bicep contour directly. In some cases added lines such as 272 as well as 271 can be projected to give even more contour information directly, and quickly such that human movement is not a problem. A mesh grid of projected crossed lines can also be used where desired.

FIG. 2e illustrates, for use with a single camera, a special, but simple, probe provided with multiple point targets. As shown a single camera 280 (connected to a computer not shown, such as a Pentium III 600 MHZ by Dell Computer Co.) is used alternatively to the stereo pair of cameras shown above. As such, as single point location can in general only be determined in x and y, and cannot be determined in 3D space (including z), except using triangulation as noted above where the camera and laser pointer directions are known relative to each other.

However, a special probe such as 285 can be constructed which has 3 or more spaced points 286-288 on it which can be identified by the camera 280, and the attitude and location of the probe determined. Even more specifically, where the location of the tip 290 of the probe with respect to the determined targets is known a priori, the tip location 290 can be determined in space in this manner. Thus if the tip 290 is placed by the user 291 on a portion of his body such as the stomach 294, the location of the point touched 295 in 3D space with respect to the camera 280 can be determined. And thus successive positioning of the probe tip on different portions of the body can indicate their respective locations to the computer, and the point location 296 on the displayed model 235 can be represented.

While TV cameras have been used to illustrate the invention, it is noted that other sensors such as ultrasonic transducers or inductive devices can be used (albeit less desirably in most instances) to input data from the location say of a persons finger touching either the material or the screen. An example of such a device is the FreeD ultrasonic unit marketed for gaming applications by Pegasus Technology, (Holon, Israel) which utilizes 3 microphones to triangulate on an Acoustic source on the persons finger. In FIG. 2A, if these were used, cameras 220-222 would be microphones, and the LED of item 246, for example, would be an acoustic source.

In my experience, ultrasonic devices work in the invention, but they are not in general as accurate as the optical ones, nor as versatile or data intensive, nor as potentially inexpensive.

As pointed out in co-pending applications by the inventor, optical sensors with PSD detectors to detect LED or other Artificial target images can be used instead of TV cameras. These generally provide faster data inputs, but are single purpose typically, and cannot be used easily for the many other applications that TV cameras can, including the finding of edge features of the clothing, or the detection of clothing patterns or colors (where Color TV cameras are used). Such detection of color or features is a useful added feature if input to the computer of existing clothing having such features is desired.

The invention may be used to input detail on an existing piece of clothing owned by a person, in order to aid in determining the costs to alter it to a new shape of the same person, or to make it fit a different person, such as handing down a wedding dress to ones daughter. As another example, data from an item purchased, lets say by mail order, which doesn't fit, can be inputted to a remote computer to develop a plan for the alterations needed, where for example, the manufacturer or vendor could then authorize a course of action, such as locally fixing the item, sending it back or whatever. Such data could alternatively or in addition comprise a picture or even video clip of the person in the outfit, say for example taken from various angles and further including as applicable, voice data as well.

It is noted that using sensed data from the person, the model shown on the display screen can also be generated by computer 230 or another computer to have an orientation on the screen similar to that of the person standing before it. Not only can the orientation be similar, but also in the extreme, the positions of hands, feet, head and the like be similar, approximating the actual appearance in a mirror of a person—who may even move around and change the appearance as a result (in this case with the model changed to suit).

FIG. 3

FIG. 3 further illustrates data input and display using the invention, also illustrating logistical and commercial aspects of the invention. A display in ones home or elsewhere is preferably, but not necessarily, on a life size screen, and the digital image produced may be created or modified using an ability to touch ones self or ones digital self (and future self) represented on the screen. An interactive session of a user employing the inventions method of inputting and providing dynamically variable choices of alterations or styles, or even entire lines of garments is disclosed.

It is noted that a touch screen can also be used as input, and novel types thereof are disclosed in references above incorporated by reference. For this application, the display is preferably located in ones home and is preferably a life size display, today created by a rear projection system. The digital image produced is not only created but then modified using an ability to touch ones self or ones digital self (and future self) represented on the screen.

With the advent of affordable large screen displays, the digital model created can thus be displayed "life size" even in a persons home, just like looking in a mirror in a clothing store, but instead seeing a "digital You", in a particular outfit, and possibly with means to modify your appearance (as disclosed in reference 8). Because it is all a simulation, one can "try out" not only different clothes in a lifelike way, but also see the effects on your appearance in one article or another, in one size or another, of different courses of action, of different alteration strategies, and different cost strategies regarding alteration versus custom tailoring and the like. (see FIGS. 4-7 below).

For example consider FIG. 3, which illustrates a touch screen based embodiment of the invention in this aspect. User 300 looks at the rear projection screen 305 which has been converted to a touch screen using the invention of some of the references above. More particularly, the screen is illuminated by a micro-display projector 310 (such as a DLP based projector by In-Focus company), capable of providing a bright digital and life-size image on the screen, of the digital model 315 of the user (or anything else for that matter). This is a dramatic way of getting the point across as to what one would look like in different scenarios, as it is like looking in a looking glass, so to speak. The projector 310 and the touch screen readout (of whatever type used), 320 are controlled by computer 325.

Indeed, one can touch the digital model 315 of ones self (or if desired of someone else), just as if you were a "tailor", and you were working on tailoring your own clothes. This allows you to tuck, snip, cut, pinch, and other wise modify either the clothes on the model (feeding the data back into the clothes model data base for example) or the human model underneath the clothes for example, with a "what if" situation, that if one lost just a little weight, or more specifically, if ones arms were just a little less fat.

The data can be taken ideally with either a touch response screen for example that of reference 2, or TV cameras watching the humans hands or objects in the hands, or both—just like a tailor uses to touch and gesture (and as shown in other references above). But it can also be inputted by voice command and known voice recognition devices and programs like IBM "ViaVoice" (e.g. with a command "take in the waist", or "make arms less fat"), or it can even be typed in on a keyboard or other data entry device.

The modification of the digital model including its pose, shape, etc can be in any suitable way programmed in to the computer, and can be for completely different purposes. In addition the digital model, where desired, can be a model of someone or something other than the user. One can indeed, just like a tailor, work on someone else's clothes, or like a masseuse, on someone else's body (digital, that is). There are numerous games that can surround some of these aspects of the invention, some of which were disclosed in the co-pending applications.

The user in this example, on seeing the digital model of themselves in a particular pants suit, notices the collar is too tight. She then signals the computer, in this case by touching with finger 330 the "virtual" material 335 in the neck area displayed on the touch screen 305 in a manner to suggest an alteration, weight loss regimen, or other alternative that would allow her achieve a better fit. She can tell the computer via a voice recognition based command, what she wants done—e.g., "take it up". In return, the computer program itself could redisplay another suggestion to consider, to the chosen garment. In this manner artificial intelligence can be added, and not only can the suggestion be made, the 3D model can be reconstructed to illustrate the change desired or suggested. Clearly the waist, buttocks or any other region could be similarly displayed and dealt with.

On command, the computer program then alters the Dressed model accordingly, displaying, for example, in box 340 on the screen, a listing provided from computer 325 of the suggested alterations and their costs and allows the user to make a value judgment as to how to proceed. The data can in addition or alternatively be outputted as voice data from the computer via speakers 370, which can at other times be used for example, to provide restful music other information. If no alteration makes sense, the computer program may alternatively suggest the closest workable outfit that seems to be of the same type the customer desires. Similarly, in the case of body modification due to exercise or weight loss, for example, the computer program can alter the model shape accordingly. In this example, in box 340 on the screen a listing could be provided from computer 325 connected to internet derived data source 326 for example, of the diet and/or exercise plan it takes to get there, and allows the user to make a value judgment as to how to proceed. As before, the data can in addition or alternatively be outputted as voice data from the computer via speakers 370, which can at other times be used for example, to provide restful music, workout video information, or other useful information In one case the user may say, that they cant achieve the bodily results needed to fit the particular outfit depicted in time, and that she would like to try on another outfit, or another size of the same outfit. Or she may say that she is willing to do buy that outfit depicted, if the needed alterations don't cost too much, or take too much time, in which case the computer is optionally asked to compute the cost for same, perhaps by a voice command from the user using microphone 360, or by entering the data via a keyboard or other conventional means.

If all looks ok, the user could be induced to place an order, for delivery, of the garment desired.

It should be noted that the image displayed in FIG. 2 or 3 above may be of someone else, whom you are helping, with the touch being provided by someone who is not the person whose digital model is being presented. This helper can even be remote from the user. It is noted too, that touch screen 305 may optionally be equipped with TV cameras, such as the stereo cameras 391 and 392 located at the corners of the screen as shown, and as disclosed above, for inputting data from the user or other purposes. In addition, a microphone such as 360 is very useful for obtaining voice inputs to help define the action in changing the model, for example by using a voice recognition program such as IBM Via voice to recognize say the historic clothes alteration commands, such as; Take in; Take out; Take up; Let down; Let out.

In the case of weight loss planning, other ideas can be tried as well. In another session the same or another user may indicate that they want to really slim down for summer, and begin trying on virtual bathing suits, so to speak. A series of modifications to the shape are suggested as desirable by the user, in this example by touching the screen in the areas to be trimmed or expanded on their digital virtual body model, and in each case a suitable diet and exercise plan is presented to help the actual body arrive there. When a plan is reached which the user thinks can work, in the allotted time, the computer program resident in computer 325, or remote source 326, then may suggest, if desired, a number of swim suits of this size or which can be easily altered or manufactured to suit. Clearly at this point, the user could be induced to place an order, for delivery in the future, of the garment desired.

However, should the diet/exercise regimen not be followed successfully, or otherwise not achievable, data can be sent to the clothing maker in time, to schedule another size for example. (assuming this option was chosen). Such data can be automatically transmitted, by having an update session every week say using the data input devices of the invention or even manual input to the clothing company's data bank. Similar to the point illustrated above, in the case in FIG. 2e, a probe tip can alternatively be placed on a display screen such as 225, on top of a projected image location known with respect to the camera, such that a point 296 on the displayed image 235 can be identified as well.

It is noted that 2D models can be used rather than 3D models, but are not as lifelike, and much less valuable for depicting difficulties with fit. A 3D model can be rotated and looked at from various angles to see problems as they occur, as well as to get a better feel stylistically for a fashion item in question. That said, the invention herein comprehends that approximating ones appearance from a series of 2D camera images, which can be interacted with by simple 2D means, such as a touch screen. Camera images of the person in two dimensions can be digitally altered to reflect predicted future measurements of the person (after some diet or exercise program, generally) visible in the view in question such as front rear or side. As noted above, the person can look at the starting representation, and determines if desired, any places that they would like modify their dimensions, such as by losing weight, and indicates that to the system, which can be done by touching the touch screen in the areas in question. Or conversely, the system can provide to the user a sequence of examples showing for example the same view, in the same type of clothes (e.g. a standard blue dress), after different diet and weight regimens over different periods of time. The person can then select, often with the help of a weight watchers person or other professional (either on the scene, or remote), a desired regimen. Once selected, views in other clothes as described above can be shown if desired as well, to build reinforcement for undertaking the plan.

In another example, the client/user may indicate that they want to really slim down for summer, and begin trying on virtual bathing suits, so to speak, using the invention. A series of modifications to the shape are suggested by a computer program through a loudspeaker or on a display, as desirable by the user, in this example by the user touching the screen with his finger just as finger 330 is used to touch the model on the screen above in the areas to be trimmed or expanded on their digital virtual body model. In each case, a suitable diet and exercise plan may be presented to help the computer data base body arrive at the intended shape, typically in a particular virtual bathing suit selected (constituting the dressed body model).

When a plan is reached which the user believes will work, in the allotted time, the computer program then may suggest a number of swim suits of this size or which can be easily altered to fit or manufactured to suit. Clearly at this point, the user could be induced to place an order, for delivery in the future, of the garment desired as has been noted previously.

However, should the diet/exercise regimen not be followed successfully, or otherwise not achievable, data can be sent to the clothing maker in time, to schedule another size for example. (assuming this option was chosen, and assuming an order had been placed). Such data can even be automatically transmitted, by having an update session every week say using the data input devices of the invention.

FIG. 4

Figure 4:
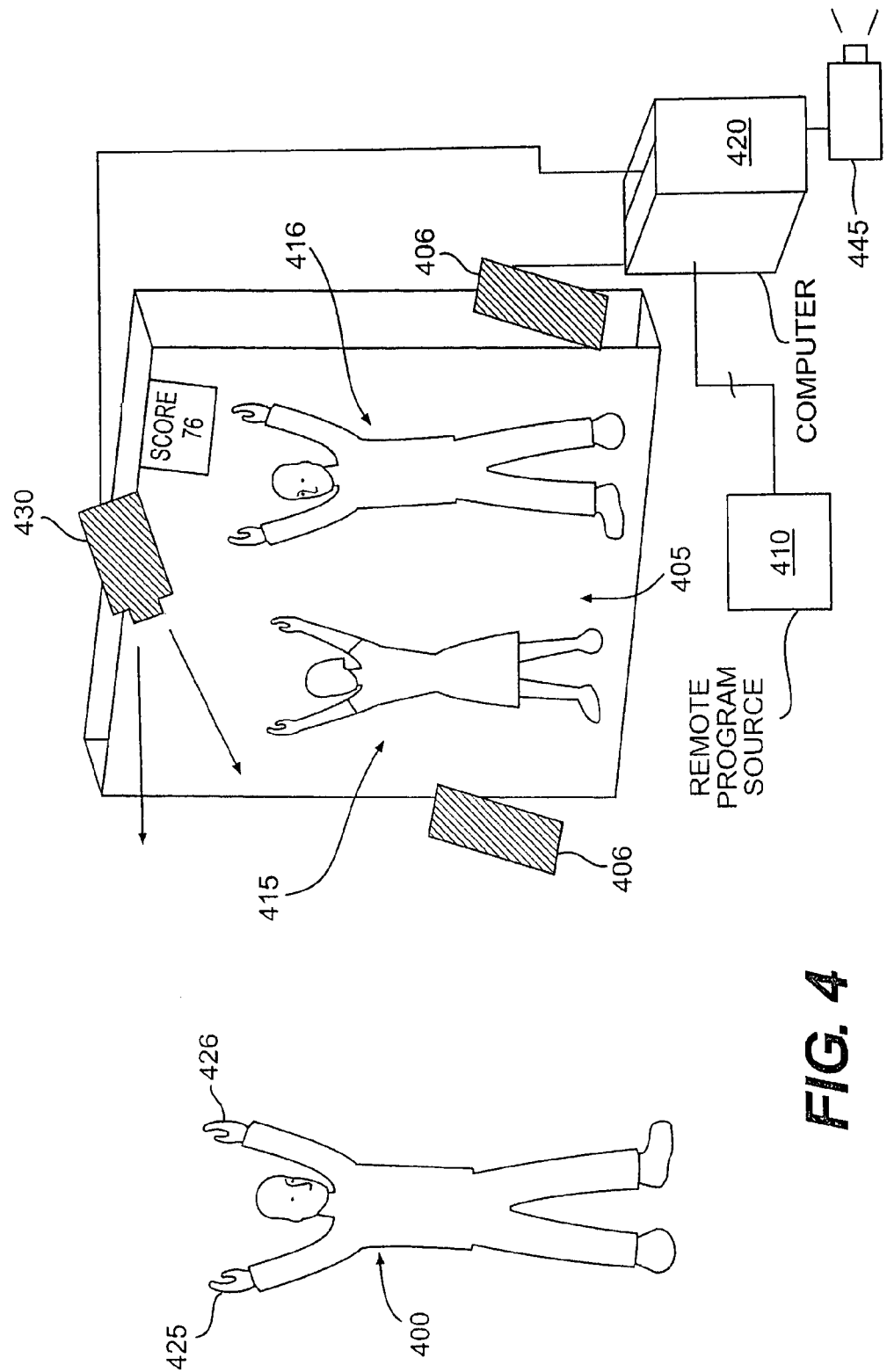
FIG. 4 is an interactive session of a user employing the invention, also illustrating clothing related logistical and commercial aspects of the invention

FIG. 4 illustrates an interactive session of a user employing the invention. For example, user 400 in front of computer display 405, has made a choice which causes the dressed digital model 415 to look a certain way. The model is compared to criteria in clothing data base 410, and a result obtained which is used to determine the fit of the clothes on the model. A second model such as 416 can also be displayed on the screen, as is discussed below.

For example, if the pants whose dimensions are contained in the data base are a length which is within a band 2-3 inches above the ground, when fitted to the digital customer body model to form the dressed digital model 415, with the waist at the waist of the model, plus or minus ½ inch say, the trouser length could be considered to fit, and an output signal, such as a computer generated voice on loudspeaker 406 could be programmed to say "nice pants length", or some such. A knowledgeable fashion expert would be the person entering the criteria for determination, based on their experience in the trade. Expert system programs, if desired such as LISP or Prolog could be used to aid this activity. If the pants length was outside the limits, another pants size could be suggested, or an alteration suggested if feasible and its price given if desired.

The same would be undertaken for all dimensions of criticality with respect to the 3D model of the user, and the results reported. In addition, an over all result can be computed, based on all of the individual results, for example if all within tolerance, it might be programmed to say, what is often said in stores: "Looks good on you"!.

If only one dimension, lets say at the hips, were out of tolerance, the program could call up from computer memory the words, "Looks good, but tight in the hips", (or loose, if oversize there) and suggest an alteration or some other action to solve the problem. If an alteration wasn't practicable, this could be stated, and the customer encouraged to pick a new size, or to choose a semi-custom fit where this portion would be cut especially for them (or pieced together from a version of a larger size). The tolerances could be on an individual measurement basis or on an over all basis—i.e. compare the clothes dimensions to the customer body model, and if any dimension is too close to the other, or too far, some problem is assumed, for example. However, purposely baggy styles would not for example, easily fit such a strict criteria.

The large screen makes it more realistic, and speakers provide sounds transmitted from the program source which encourage activity—even computer generated sounds like "Really looks good on you", or human assisted sounds (with an on-line personal fashion consultant), or something taken as a direct input from the camera system which could identify that the users choices and actions were desirable.

The invention contemplates optional display of the digital model of more than one person side by side e.g. 415 and 416, for example:

You and a friend.

You and a plurality of friends, the others remotely located with data files transferred over the internet or otherwise.

You and yourself from a stored image done last year (to show change in your model and your clothes size fits. Many people compare themselves this way routinely). This could include a dressed model from last year, say in the same outfit for comparison purposes, or it could include your body model of last year in the same out fit as this year. And these are just a couple examples.

You, but side by side in two different outfits, or 3, or 4, and so forth. This is a lot faster than trying on 4 outfits in a row, and trying to remember which looked better on you.

As pointed out above, it can be 4 versions of you, with the same pants but of different waist size (again as noted above aiding the visualization of different alternatives).

And so on.

A possible advantage of the invention is that customers may be much more likely to place orders for clothes in the future, somewhat like the layaway plans of yore but vastly more effective for both manufacturer and consumer. You see what you like, but can be in next seasons designs and your order ahead of time is of tremendous advantage for the manufacturer who can tailor his production accordingly, knowing he has firm orders in hand (likely with some modest cancellation or change fee—which itself could depend on the garment price offered). Such orders for delivery in the future can also be projected as a result of the diet/exercise aspect of the invention as well.

The future orders placed, can, if desired, be further updated with size, (and if desired or allowed, color or pattern) data from the customer using the direct computer input of the invention. Such up dates could be economically made, from the comfort of one's home, right up until the point of manufacture at little or no added cost. Worries then about ones size in the future, and the apriori knowledge of garments design in the Future are, with the invention, not limits to purchase, a major benefit for both manufacturers and consumers too, in terms of getting the latest styles at the earliest time. This fact alone could change the whole way in which clothes are marketed to some degree.

It is also noted that once a agreed on body model is established by customer and vendor, buy-off on clothes purchases by the customer is on the dressed digital model, and changes made to any initial design are known. The responsibility for the garment then can be largely transferred to the customer, other than workmanship and the like—a significant advantage.

The customer can make inputs to his body model, and the vendor (if the model is resident there, as is probable) can modify the customer model whose effect can be verified by the customer. And the customer using the invention can make a scan of himself or a zone on himself, and see if a size change on the model corresponds to what he would believe. And he can physically be displayed the new dimension (e.g. a waist size, or sleeve length, which he can then verify for him self with a tape measure, for example.

We can also consider FIG. 4 to be illustrative of an interactive session of a user of the invention relating to motivation for a given diet or exercise regimen, and employing automatic computer inputs of the invention, also providing dynamically changing data during exercise, which further allows one to see the effects on ones appearance of continuing a given regimen, or changing plans.

As pointed out previously, the system of the invention can provide either locally via storage media, or remotely via internet downloads, what is commonly known as a "Workout Video" to the user, but in this case tailored to the users dietary or exercise needs, and capable of receiving voice, position and movement inputs from the user, even dynamically where automatic sensing is employed, such as in FIG. 2.

This dynamic nature allows the workout video to be individually tailored, and even moment to moment paced for the user—just as if an instructor was present, who might say "you're not moving your arms enough", "go faster" go higher", etc. If it goes too fast for comfort, the user can ask that the video slow down, and the video source respond accordingly so the users don't get discouraged. Rate, extent speed of the video and music with it, choice of music with it and many other factors can all be called up on demand, and in response—automatically—to the users own actions.

A large screen display makes it more realistic, and speakers provide sounds which encourage activity—even computer generated sounds of encouragement like "way to go", or something taken as a direct input from the camera system which could identify that the users movements were good.

For example, consider in FIG. 4 a different scenario, in which a person 400 is doing a workout in front of display screen 405. Input video digital images, such as man and woman exercise instructors 415 and 416 are provided on screen 405 together with appropriate sound on speakers 406 from a remote source 410 connected by computer 420 via the internet. (assuming a high enough speed data transfer link, to allow a remote source to be changed subject to inputs generated locally). For example as user 400 lifts his arms in the air, his hands are sensed in their peak positions 425 and 426 by TV camera 430 connected to computer 420. The positions in this case are just registered in X and Y, in the object plane of the camera, with no attempt to determine range, z, from the camera to the persons hands (possible with the "3D" stereo camera arrangements of FIG. 2 and other figures).

The X and y values determined and the rate of change therein if desired, are reported from the computer 420 to the remote program source 410 (which could be resident alternatively in computer 420), which then can compare them to norms for that section of the work out video being presented—perhaps as well considering pre-entered data into the computer and thence to the program, of the person, such a age, weight, stature, starting condition, and medical issues if needed or monitored such as heart rate.

The program can then dynamically be changed, to go faster or slower, change programming entirely or whatever as a result of the input data and the dynamically changing data of the person, in this case his hand position and/or rate of change of position. And as mentioned, data can be fed back to the person as to how he is doing, both by voice generation in the computer, or by visual display on the screen, or both.

In addition, a score can be generated, just as if it was a video game. For example, a computed score for having the most motion, the most rapid moves, the most acceleration during the workout, etc. and this score can be compared to previous scores of the user, or to scores of others nearby or around the world using the same program for example. Such a score "76" is shown generated by computer 420 and provided on the upper right hand corner, in this case, of the display 405. Scoring can be based on an integral of moves, a mean, or any other tally desired. Some scores directly relate to energy expenditure and weight loss, while others could be just for "fun" so to speak.

The invention thus includes a method of providing dynamically changing data during exercise which allows one to see the effects on ones appearance of continuing a given regimen, or changing plans. It should be noted that datum's can be provided on exercise machines to enable their positions and movements to be also entered into the computer, to calculate activity of a person using them.

The ability to see depicted life-size or otherwise ones own model under different scenarios that would effect change on the model, allows one to do interesting tricks besides. For example one model could be on a screen in front of someone working on a treadmill. As the person exercises more, his own digital model could changes to indicate the improvement he will have if he does it every day at the same rate or incline, for example. The treadmill is also a good example, where a walking video can be portrayed to the user, and his movements monitored with the invention as well as his pace, as he navigates a path shown of the video. The same holds true for riding stationary bicycles, and other forms of exercise machines. Indeed it is anticipated that people will record their own videos, such as a home made workout video perhaps inputted as shown from home camcorder 445 to computer 420 which can then be used as sources for others around the world who might like to participate with them. Even more applicable perhaps is a biking video taken by one user going around his neighborhood say, which acts as a social event with others who can also partake on their stationary bicycles with him, by sharing the video signal over the internet It is noted that a useful place to set up the invention is in a gym. For example, another interesting application of the invention is to perform some of the above procedures while actually exercising, both to kill time, and to provide motivation for improvement. For example it is customary for many to watch TV while exercising on a treadmill for 20, 30 minutes or so. This time can be spent using the invention, which can present the images for example on a screen in front of the treadmill which can even be touched by the user if desired, while walking. One can also sense the user with cameras, similar to what has been disclosed elsewhere.

As another example of what can be accomplished, an illustration is made of a weight lifter using the invention, in the home or gym. Guessing what's important, for those who lift weights, the big attraction may be the digital model of their biceps, which respond to camera views of their weight lifting.

For example, in another use of the same system of FIG. 4, a weight lifter in front of display 400 could lift a barbell, with camera 430 viewing his actions. The computer 420 provides via loudspeakers 406 inspirational sound and image for the weight lifter, and, as he lifts the weights (not shown for clarity), the TV camera and image processing program resident in computer 420 can be used to identify the amount of weight lifted (by the number of weights on the barbell for example), and the height that it is lifted, and how often it is lifted. This data can be used to calculate the work performed, and other relevant training factors. And such data, plus a pre-entered knowledge of the person, can be used to predict the eventual outcome of the activity, or to predict the eventual size of various muscles etc. These muscles can be simulated on a digital model of the weight lifter as described above. If the activity is unsafe (too much weight, tilted bar, etc) the computer can advise accordingly as well. Too much weight after too long a time of exercise would be one such example.

Clearly, the TV camera can be used for digitization of the activity of a large number of exercise activities for the benefit of the user. The display does not have to be a digital model and the modification thereof, but could be any other kind of motivational presentation for example. The camera computer combination can be used for other beneficial activity as well, such as assuring that movements are not beyond preset or calculated limits or time integrals related to endurance and the like.

From a cost point of view, it is clear that the same computer display, camera systems can be used for a variety of applications, thus making each by itself relatively in expensive. Indeed the Screen (the most expensive item, typically) can be used for normal TV show watching or internet activity as well, or for control of the home—if a touch screen.

FIG. 5

FIG. 5 illustrates several methods which address weight related dimensional input issues to the digital figure model (also discussed in co-pending references incorporated by reference), and as well illustrate how the invention may be utilized to provide data as to ones future appearance.

FIG. 5 is a Block Diagram similar to that of FIG. 1 of how the basic invention is utilized to provide data, in this case as to ones future appearance. This can be used solely for the purpose of prediction of ones future look with no clothes on, or in a given set of clothes already on hand, or in an interactive "what if" tradeoff analysis, with a selection of clothes and diet plans for example.

In general for this purpose, the body is measured, not just for its dimensions that relate to fit of clothes per se, but also with respect to certain dimensions and other medical factors that allow prediction of the effects of exercise and diet (to achieve weight loss or gain) on the ability to change ones shape. These can include measurement of fat at the waist, arm girth, and the like, as well as medical tests whose data from laboratories or elsewhere can be entered if need be. Height, weight, age, general stature, and other factors—including any special case issues, are also generally desired as input.

The invention contemplates that the actual procedure can vary. A typical embodiment would do the following when used for prediction of future shape, without clothes; In first step 510, the user enters their dimensions and other information as called for by the program, which may include, for example:

Dimensions of key parameters of the persons body necessary for establishment of a minimum 3D model. For example, some are mentioned above per the Rose patent.

Physical body health related dimensions and other applicable parameters such as % fat mass, stature, etc.

Other physical health related data, including Medical history as applicable.

This data is then provided to the program, which generally is located distant and accessed over the internet, but could alternatively be on DVD disc, CD Rom or other local storage medium, or downloaded thereto off the internet for example. A model 515 is then created of the person today. The model can be a 3D digital model created by known means, for example using a 3D solid model package such as "CAD-KEY". Such a model is shown in the Textile Technology article referenced above. is contemplated that the entry of data can in some cases be automatic using for example, features of the invention, or the inventions disclosed in the co-pending references The program in the second step, 520, then asks one or more questions related to the effects and goals desired, e.g. Lose 10 pounds, or fit size 12 dress (in the latter case, it would be desirable to enter ones present size). Or lose a couple inches in the buttocks region, or whatever. Numerous other variables are entered 521, as need be, which variables can be traded off, such as; Calories per day; Type of food per day or week; Type of exercise; Type of exercise machine, if any; Drugs, if any.

To aid the conceptualizing of this, a display of the "Before" model 515, and an "after" model 525, of the person is created from the measurements, and a video image of the users head 530 superposed if desired, as in simply done in the U.S. Pat. No. 4,261,012 patent (Maloomian), or with more views taken as is desirable and taught by Rose. More precisely a scan of the persons head may be taken with a 3D scanning system which may also be used to capture a large number of the persons body dimensions. It should be noted the face and head scan may not need to be performed as much as the ones taken to updates the model in more rapidly changing regions of the body with diet or exercise, such as the waist. The model at this point more or less looks like the person, and the effects of the various activities can be seen using programs created to model the effect thereof.

The program then can compute or suggest, using a data base, a dietary and/or exercise plan 535 to achieve the desired results in say twenty weeks. If that is too long, an alternate plan 540 can be requested and called up from a data bank and/or computed, and a new model 545 created to match. Or suggestions 550 made to the user as to what new less aggressive measurements to back off on achieving might be. Such data output to the user could also contain health tips including vitamins to take, and the like.

By such an iterative process, the user finally arrives at a plan he or she can live with, and the regimen can commence. If it turns out that its too tough to achieve, a new regimen for example having 100 more calories per day, or 20 minutes less treadmill time, can be requested to be computed and an alternative model and data picture of the results presented to the user.

The above points all relate to creation and display of the 3D user model in various scenarios of diet and exercise and the like. But generally, the user is interested not in what he or she looks like with no clothes, but rather in the clothes normally worn—including clothes for special occasions that one often especially strives to look good in.

In this case the invention then further contemplates the extension of the digital future basic body model above, to a model 555 with the known dimensions or other characteristics of clothes added, after selection 560 by the user from styles and sizes presented to the user. Such data would typically be provided by the clothes vendor, for example on their web site. The vendor input data is indicated at 563.

The user can now iteratively repeat in step 565 the relevant steps above, also with the input of different clothes styles and sizes, together with continual iteration of diet and exercise plan, until the desired practical health and appearance plan 570 and clothes purchase (possibly for future delivery) 575 is arrived at. As pointed out the invention contemplates method and apparatus to do all of this in private, there is no embarrassment, and the actual true and maintainable plan can be achieved.

The clothes selection step could involve an automated, or even a real human on line fashion consultant as contemplated by the Rose work. Or the online consultation could be from a personal trainer or weight loss expert. (e.g. a Weight Watchers certified person)

FIG. 6

Figure 6:
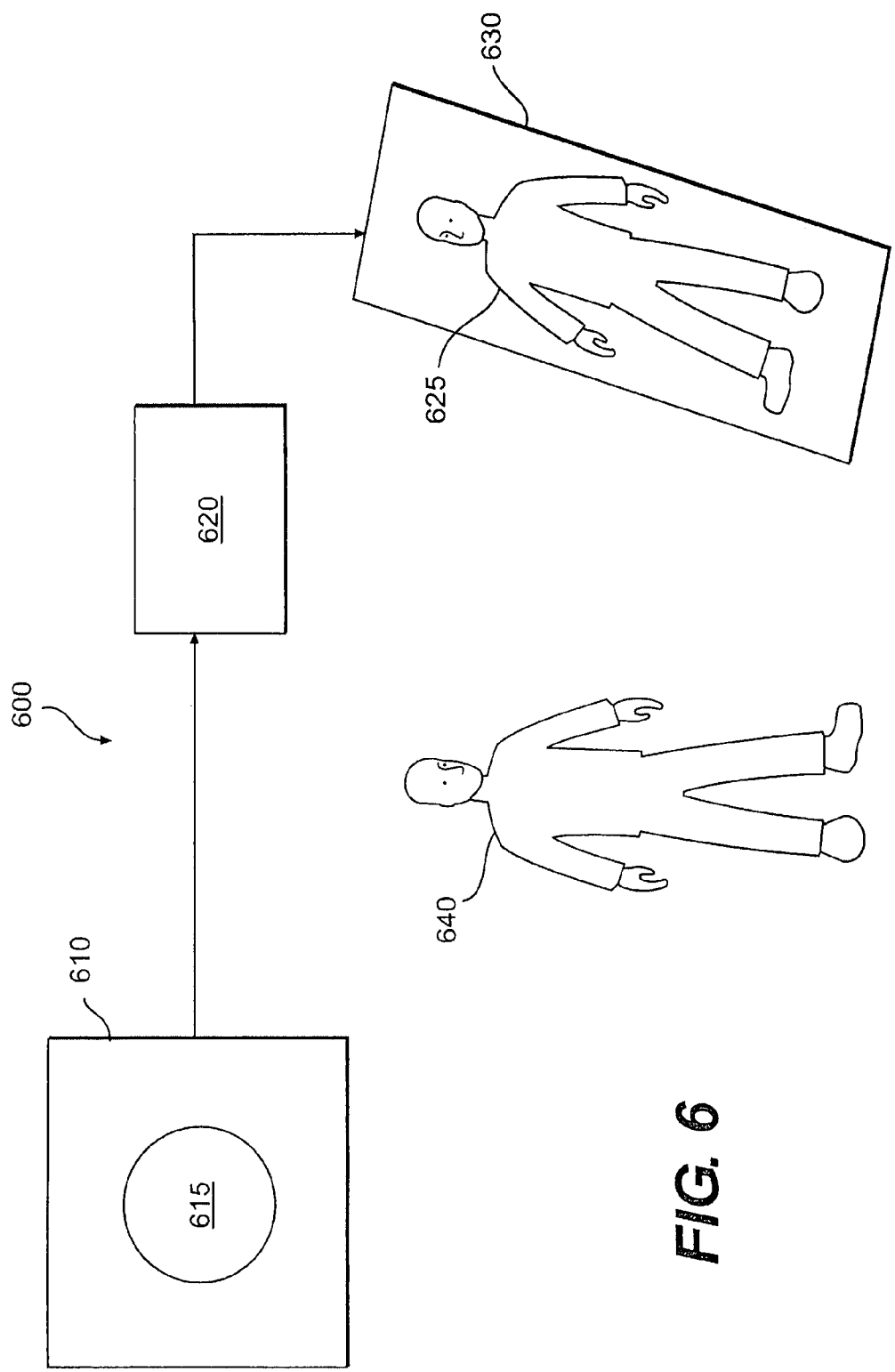
FIG. 6 is a diagram of a possible "Weight watchers" (or other organization) meeting area, using a relatively inexpensive automatic or semi-automatic scanner to obtain clients measurements. A full length "digital mirror" of the invention may be optionally provided, and data taken may be transferred to home computers and displays of clients if desired.

FIG. 6 is a diagram of a possible "weight watchers" (or other weight loss organization) meeting area 600 constructed according to the invention which may contain a relatively inexpensive automatic or semi-automatic dimension scanner 610 (for example operating on optical triangulation principles as discussed in the references) to obtain data from a persons body 615 in order to calculate using computer 620 the persons measurements and create a digital model 625 (with or without clothes) of the client person which is displayed on a preferably substantially life-size digital mirror display 630 (previously described, and provided by a projection TV) and viewed by the client person 640 at a later time for use with the invention.

This arrangement has multiple advantages for all persons involved—the client, the weight watchers franchise operator and the manufacturer. First, it provides a high level of inspiration for the client, on the first visit and on all successive visits. This in turn allows, the operator to attract and retain clients that otherwise might drop out. And the motivation is also economic, since we believe it further allows both the client and a clothing manufacturer to save money. Since the manufacturer can get an early reading of the clients wishes through the interactive process at the weight watchers site, he can eliminate middlemen and inventory, and his production of garments in say 6 months can be much more efficient, when he can make a garment ordered for delivery to the weight watchers site, or to the persons home. The manufacturer can give a substantial discount to the client as a result, and perhaps help the weight watchers franchisee to underwrite equipment cost. This then also encourages participation in the program and even allows the operator to provide incentives as well, since it opens up another avenue for providing goods and services to the client. It is hypothesized that clothes data would be provided by manufacturers to weight watcher's clients 'gratis", and that they might even pay the franchise holder for the privilege.

It is likely best to wait until the last possible moment to make the garment, as the data coming in from the client (who has preordered and desirably placed a deposit) is likely changing. If the client has failed (or is failing, as predicted from data taken at a given point in time in the weight loss/exercise program) to achieve his or her goals for achieving a new shape, and wishes to cancel, a pre-agreed cancellation charge can be charged up to just before the date of manufacture (at which time the manufacturer has purchased the yard goods material, but has not added value thereto.)

If the hardware can be inexpensive enough, as we feel it can be, then it is likely either the operator or the manufacturer or both would provide the equipment to take the measurements, associate dietary and exercise data (such as the weight watcher point system they use, possibly in conjunction with other data or input from a fitness club). It is likely a fitness club could be associated with the effort, as could medical personnel if needed—particularly if drugs of some form were involved in the plan.

While discussed here in the context of location at a weight watcher location, it could be at a health club or at a retail store. And in the future, as price comes down, all steps can be in ones home, benefiting from the internet or other remote data transmission and analysis. In time, the complete program for everything could be resident on ones own computer, and perhaps all clothing data too (after receipt from the manufacturer).

Returning now to the meeting area 600, on the first visit to the facility, the client s present dimensions measured, their digital model created (and clothes to fit their present model displayed on the present model, if desired). Then a first regimen suggested for the client can be inputted and the results displayed on the future body model, probably dressed in some choice of clothes, which then can be fitted digitally from the manufacturers data base and downloaded to the operators location. This initial viewing and fitting could take as long as practicable, to give the new client the view of themselves as they want to see themselves in the future, and to sufficiently inspire them to attain whatever dietary and exercise goal they set.

After "N" visits (N being 1 or several, typically, the choice being made by client and organization), the client is again re-measured and the new data is used to predict the future shape of the client, say at the same desired future point in time (or if desired, an alternate future point, say two weeks later after more benefit of diet). If the results are less appealing, the client may decide to work with the weight watchers operator on a new regimen to make up for lost time so to speak, or to simply digitally try on clothes that are effectively a larger size. The client can, in one business scenario, change any purchase request previously given the manufacturer at this time (as for example to size, but also color and so forth), or cancel.

To aid the user in visualizing themselves, one can provide a three display system, that, just like a fitting mirror today in a store, shows three digital views at once so to speak, having the advantage too that one can show a complete rear view on one screen, a front view on another and a side view on a third—but unlike the store case today, all screens can be if desired in front of the user, since the display is created in the computer. Such an arrangement is nice, but expensive, and not actually needed, as one can show any view desired in succession on the screen—front, back, sides, angled etc. even oblique views from the top, or bottom.

And as pointed out above, one can show "before" and "after" body model, or dressed body model, presentations (predicted as a result of any given course of action), either in succession, or side by side. And one can look at the predicted model, and suggest that from a clothing perspective, you would like more material to be removed say from a given place. Or in the case of the users action themselves, if they wanted to lose or gain more body matter in a particular place, course of action to achieve that, where practical, could be provided the user in the form of a printed document or whatever, and the future body model predicted using that data, as well as any dressed version thereof using the clothes data base.

While the above discussion has focused on carrying out the dimensioning and feedback at a weight watchers meeting room, this is not the only venue. As noted it could be in a retail clothing store, a sporting goods store, a fitness center/health club, or even a car dealer who would use this feature to build traffic. But as pointed out above, and in our earlier '797 application (to which this application is a continuation in part), it can also be in the home, which has a big advantage for those who do not want to discuss or demonstrate their body shape with others. The invention comprehends that the special equipment needed for full utilization of the invention, if desired, could be rented from the weight watchers group, or from a store or whomever. This is particularly possible since the time of use may be for a specific limited time frame, such as 6 months. (the well known desire after the Christmas holidays to get slim by summer, for example). With this done, the dietary and other advice provided can all be done over the internet or by other means. As the price of equipment becomes less, and/or usable for other purposes, permanent home installations become possible. A full length digital mirror provided by a projection or plasma TV, can, when turned sideways, become an HDTV for the family room for example. Some types of sensor devices used in the home to take data as to positions on ones body, can also be used for games, and so forth.

FIG. 7

Figure 7A:
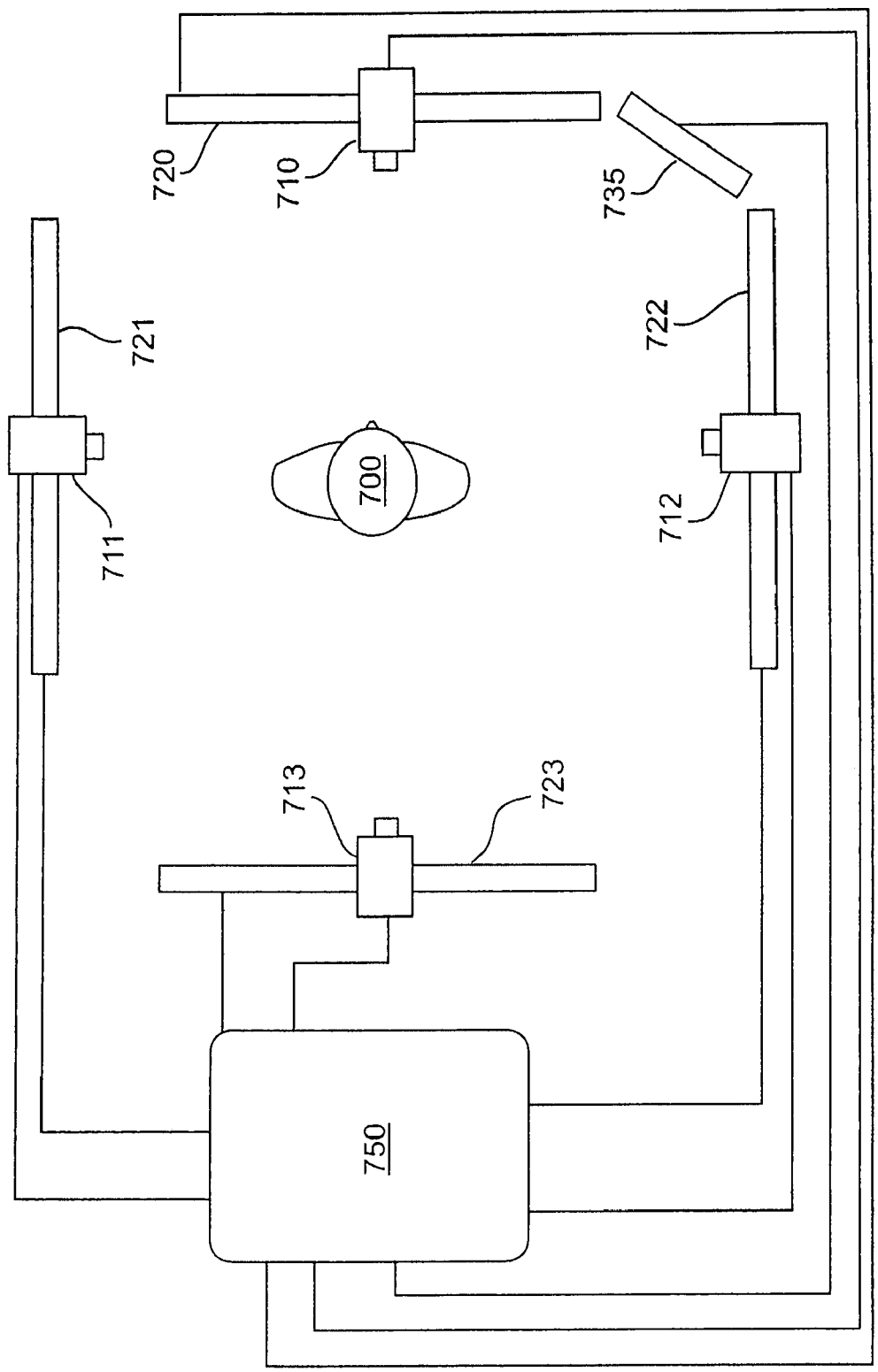
FIGS. 7a and 7b illustrate real time user assisted creation of 3D body models from 2D camera images.
Figure 7B:
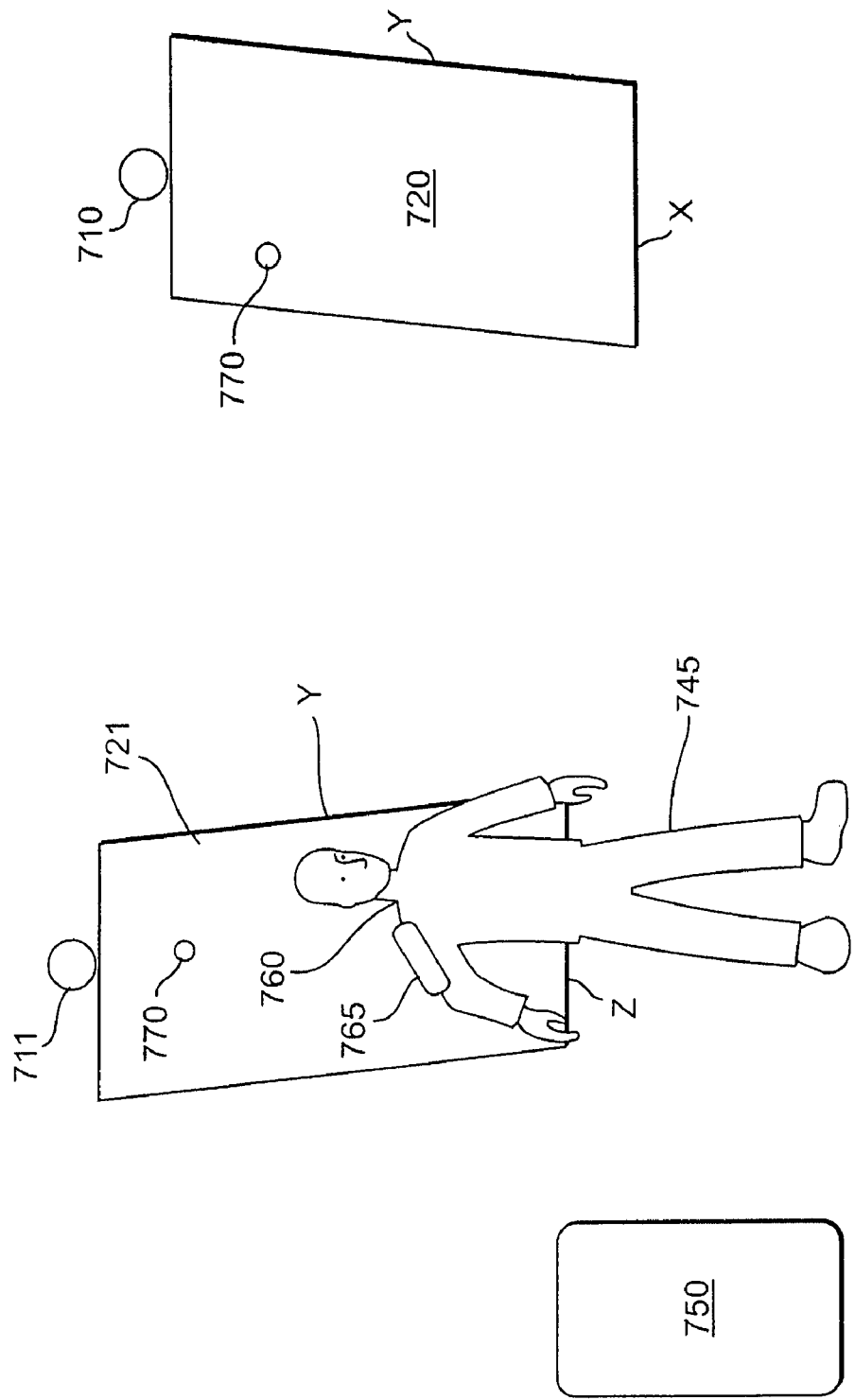

When using digital models it is desirable to not just look at one view. With a set of simple 2D views, this means switching from front to side, and likely to the rear as well. Each would be need to be shown in the future predicted shape. In FIG. 7A a simple means of creating 3D models from 2D views is illustrated which is helpful for low cost use of the invention. As shown a person 700 wishing to use the system is imaged by cameras 710-713 which take an image of the front back and both side of the person respectively. The images from these cameras 720-723 are displayed on displays such as 730-733 respectively. The displays 730 and 733 are of the front and back cameras, while the display 731 and 732 are of the side. Other arrangements are possible, and it is noted that some displays can sequentially display different camera images, or even split screen images with two camera views one display. For example the model on display 733 illustrating the digital model of the persons rear view, can be displayed on display 730 in front of the user, or in position 735 off to the side In this example, illustrated in FIG. 7B with respect to two cameras only, the user 745 facing camera touches themselves (or other wise indicates for example using a laser pointer) at key points visible to two cameras, for example camera 720 in front and camera 721 on the left side as shown Since the cameras are orthogonal to each other, the same point touched on themselves in both a front and side view allows the computer 750 to create a 3-D coordinate for that point (point x and y in one view, y and z in the second for example).

The user can assist the program by doing this at a number of points, in essence then creating a very simple 3D model from a set of digital camera views. The displays aren't even needed in the simplest case, as the user can touch themselves and the data is recorded. It is possible that using still pictures, one can also record ones voice as to which point is touched in which frame. For example a 3D coordinate point 770 can be created for the top of the left shoulder 760 of person 745 touched by finger 765 of the persons left hand. Or max hip position on left side as another example.

The cameras can record this dynamically as well, allowing the user to trace oneself in essence with a continuous string of points, building up the body model as one moves ones finger along it. And one can use two fingers at once if there are sufficient cameras. For example a user can while facing the front camera and display, touch the two opposite points of their waist, one point with a finger of each respective hand. In this case, the front and back cameras can see both fingers touching, while the side cameras just see the one on their side.

In another example, a loudspeaker driven by a computer program used to analyze the point locations can tell the user where to touch next. In this manner a model can be built up taking the minimum number of points needed by the program in question to generate the resultant 3D model (or for that matter 2D models, if such was wanted).

The invention can be used in the diagnosis and treatment of mental, behavioral and other disorders. In addition, the invention in a related manner also contains novel methods helping the mentally ill and other persons improve their quality of life by creating life-sized digital persons they can interact with.

Treatment of Anorexia and Bulimia. A previously described, the person using the invention, once their data is entered, sees them self as a computer model on a life size screen, preferably in a 3-D graphical representation. But this isn't them, it's the model. In one form of operation, the invention may then display a normal persons model, with measurements and provides a comparison of the two models. The amount needed to increase to meet the desired normal person is shown in animated movements, such as 1 month, two months etc, until one grows out (note this animated sequential presentation of future models can also be done to show ones rate of decrease due to a weight loss program). This type of presentation may help those with anorexia or bulimia to see their digital selves as against other persons (such as idolized persons) digital representations, rather than relying on real life views which are subject to interpretation. This may have therapeutic value, particularly if the person wishes to become just like their idol, who generally is not suffering from the disease.

The invention can be used to provide a digital 3D model of a partner for an ill person or other person on the substantially life size projection (or other) TV screen of the invention. This partner can be programmed to carry on a conversation with the person (who is often lonely and needs someone to talk with or dance with, or do something else with), with the dialog done remotely over the internet (for example by physiologists or other medical professionals, or from pre recorded video clips from DVD storage say, perhaps in response to questions asked and recognized by voice recognition software such as IBM ViaVoice. Alternatively or in addition, the dressed body model of the user can also be displayed on the screen, such that the dialog between ones self and others (which could be many) can be observed in the third person. The dressed model on the screen, which could be of another person, or the user, or both, can for example dance, in tune with music, and this can be a dancing partner for the user. Dance therapy of this sort is often valuable for persons who are ill and often alone.

To effect animated activity of this sort requires more powerful computers than quasi static fashion or weight applications since the whole model (or significant portions) needs to be changed dynamically, which is computationally intensive where 3D models are concerned. A Pentium 4 with 3 GHZ together with a high quality ATI or Nvidia graphics card however can do this job with simple 3D models The patient can for example, be dancing or talking with a person model depicted on the screen. The person model could be that of a family member, a friend, a doctor or whomever. This interaction could also be done in the $3^{rd}$ person, with the dressed body model of the patient also depicted on the screen, having a conversation or other physical interaction with the person model. In this case it is generally necessary to sense the position and orientation of the patient in order to manipulate the image of the patient on the screen. It might however be therapeutic to have the image driven by a computer program, which would cause the patient to then say words in response to what he saw his virtual $3^{rd}$ person self doing. For example, making a social error. This can be part of the therapy itself, and video and audio recordings of the activity of the patient in response to the visual images and sounds can be recorded for later diagnosis.

Some other implications of the invention should be noted. For one, it is entirely natural—that is what the user may do in his home, or over the internet, resembles what one does today. You see yourself in a "mirror" (depicting your virtual digital 3D image in clothes, and you instruct vocally or with your hands and fingers to someone to alter the clothes to fit (or you do it yourself). Or you pick some other clothes. And you try to do it in the most economical manner, in both clothes cost and time. The internet or other such enablers of communication and data base media, and the vast choice of styles, manufacturers and alteration possibilities (especially with the invention leading to same) allows much more efficient execution of this task, to arrive at a better fit and more cost effectively. Alternate choices presented for selection can be either manually accessed, or automatically chosen via a programmed function based on the user model, fit, and preference data inputted, and the deviations from desired results indicated by the user. And you may do all of this in the comfort, and even more importantly, the privacy of your own home.

It is expected that many weight, health, exercise, and clothes conscious people will spend considerable time in comfort of their home for hours trying out different programs, trying on virtual clothes, and engaging in workouts and other entertainment activity interspersed with their clothes selection activities. The expected weight of a user in a given regimen or activity, in pounds kilos or whatever, can be displayed on the screen of the invention along with the digital model portrayed. The various models and regimens can be stored on digital media for further use in the future. It is also noted that the same display can be used for entertainment—TV, internet etc, and thus have little added cost. And using programmable optical elements (e.g. from Digilens), or using the new Philips Mirror display one can switch between a normal mirror, and a digital display of a model. This allows one to truly feel like they are looking in a mirror!

It is not easy to predict the way in which weight is lost from the body. Each user may have a different reaction to a diet and exercise plan, in so far as how each of their body dimensions changes in the predicted future model. By analyzing, using a computer, trends in, for example, the change in one or more dimensions (for example waist size) as a function of the treatment plan and time, generally in conjunction with medical, and/or other data concerning the person, or similar persons, or other parameters or information, this prediction can be made more accurate. Alternatively the analysis can be made remotely, using data banks from other persons, such as those with similar physical characteristics, backgrounds or the like.

With suitable computer processing power it is possible to have dynamic model animation thru which one can visualize the way in which ones body changes with exercise, diet or other regimen: Such an animation can show the user how they originally (at the start of a diet program say) would have changed, versus how they actually have changed, and are predicted at the time the animation is viewed to look when they are finished the particular program regimen in question. By watching the information dynamically (effectively speeding up time, from a few months or more to a few seconds), the person may get a better feeling of the effect of changes in diet or exercise affect their appearance in the future.

What we call "Partial Mass Customization" is a unique aspect rendered practicable the invention. Today one picks clothes off a rack, tries on two or three sizes, and picks the size that fits you assuming you like the item. Sometimes you have to pick an item you like less, just because the thing you want in your size is sold out. Or you have to give up and go to another store. All this is wasteful in time of both customer and sales people. And extremely inventory dependent, and accordingly costly as well. In addition, when you find the item, it may not totally fit. The more your figure does not conform to certain norms, the more the clothing may have to be altered, a time consuming task, involving further labor and then a time delay until pickup. Those with exceptionally variant figures, are often forced to take ill fitting clothes (e.g. baggy) just because nothing else can fit within reason.

Because of all these problems, the possibility of mass customization has been studied, as pointed out in the introduction to this patent application. In this scenario, each persons exact measurements would be inputted to a program, which would then cut the cloth in accordance with these measurements, and the garment would then be sewn, or otherwise manufactured, and delivered, possibly within a few days. This is just like tailor made clothes of 100 years ago, but at affordable cost due to technology advancements. In some circles it is viewed as "the future".

There are two problems with this. Delivery is relatively long (though not impossibly so), and what if it doesn't acceptably fit, for whatever reason? Who then fixes it? If unfixable by whatever standard, is it resalable to others? What the invention herein optionally proposes, is an in-between situation. It works like this, in one example:

The customer orders an article of clothing which is preferably displayed to the customer on a digital model of the customer. At this point the customer can clearly see, in some ways better actually than in a store mirror, due to the better vantage points allowed, and computer aids possible, just where the garment doesn't look right, to his or her tastes (virtually like the tailor in the store, saying "hmmm, I think we should take out the waste a bit, don't you think?", or some such). In addition others in the household, who otherwise wouldn't have been able to take the time to assist in shopping, can also peruse the digital dressed model (also stored for later viewing, if more convenient) and give their opinion.

At this point the customer and friends if applicable, can identify the problem in the waist (or other area), and signal the computer. The computer program then calculates effecting such a change, and redisplays the recalculated digital dressed model image—as if the change had occurred. The customer then says no, only half an inch, etc. And so forth, iteratively until the garment looks right. Or the computer can just display 4 images, each with a waist size a half inch apart (equivalent to trying on 4 sets of pants in the range 36 to 38 inches waist for example).

Once decided (also as to fabric, color, etc.), an order is placed and the garment made. But in this case, only the portion modified has to be customized, and this can be done manually or automatically via alteration. Or it can lead to a selective assembly and manufacturing process where only this portion is changed in its production. Where only an alteration process is involved in adapting a given standard dimension garment to someone whose dimensions vary in certain areas, conventional manufacturing techniques and distribution systems of today can be used for the most part. The actual alteration can be done at the factory, or more locally at high volume (and lower cost) alteration centers, or even in a "do-it-yourself mode, in your own home.

Take the pants example of FIG. 4. A manufacturer could ship all pants to the local center with pants un-cuffed, with this work done locally—(pants of un-cuffed lengths are relatively the norm today and are being used here only for illustration purposes, however the invention dramatically shortens the time involved in this procedure and reduces its cost). With the customer order of a given length, this part of the manufacturing process of the garment would be completed, and the pants delivered directly to the customer. Clearly this could have come from the more distant manufacturers plant directly as well as from a local center.

In a more exotic example, the pants could be shipped to a local center precut to length, but not sewn in the waist area. In this case, according to the customer dimensions inputted to the computer system, the pants might be chosen first for length, and then sewn to fit the waist, and if desired, the buttocks or thighs of the person ordering the clothes. The design of the garment would have to accommodate this activity (leaving extra cloth in certain places, for example).

Clearly all of the above could be done, with the pants also cuffed to length at this stage as well. There are many combinations of procedures also which could be optimized for any given type of apparel. At the extreme end, one could even begin to cut out (say using a programmable Gerber cutter for example) certain component pieces of a garment especially for the customer using the dimensions of the customer body model or variations suggested by the customer in the Dressed Model.

Taking this to its logical end, if one individually cuts out and assembles a garment using the body model one has a completely customized garment such as talked about in the various mass customization articles in the textile trade, and as exemplified in the references. But only in this invention to the inventors knowledge, have the other two issues of such extreme customization been addressed, namely;

The use customer suggested changes of the Dressed Body model to act as further the input to the manufacturing program plan, and The use of selective assembly of precut pieces, with alterations as needed, to in effect approximate a full customization taken from a body model (and further having the advantage 1 above).

Perhaps the most compelling argument for local alteration, is the question of returns. The customer in effect, is "buying-off" on the digital dressed model. This is more risky for the seller/buyer than today, where the buyer buys-off on the actual garment, with alterations he personally commands. But it is less risky than ordering a totally custom garment.

If the clothes don't fit to satisfaction, a local alteration point can also act to fix them, after delivery, if complaints result. And if they are unfixable to that customers satisfaction, they at least can be resold to someone else somehow, as they are a standard size with some change only. And since they are duty paid, if imported, customs costs if any are reduced If the alteration aspect of the invention is done locally, due to local labor content.

The risk to both seller and buyer is lessened if only small, known types of changes are made in standard garments. Thus the computer program selecting clothes would attempt to steer the purchase to such a situation. This can be done, for example, by pricing large numbers of changes and/or complex changes commensurately higher. In practicing the invention, manufacturers might produce an extra number of some portions of the garment knowing that certain areas according to the invention would be more likely to be modified than other areas. Note in the partial customization process disclosed herein some alterations might be allowed, others which are too difficult, not. Also the computer of the system at the manufacturers or vendors site, can calculate the cost of alteration or customization so customer can see the price of his wishes.

Alternate choices presented for selection can be either manually accessed, or automatically chosen via a programmed function based on the use model, fit, and preference data inputted, and the deviations from desired results indicated by the user. The expected weight of a user in a given regimen or activity, in pounds kilos or whatever, can be displayed on the screen of the invention along with the digital model portrayed. The various models and regimens can be stored on digital media for further use in the future.

It is noted that the same computer display and camera systems can be used for a variety of applications, thus making each by itself relatively in expensive. Indeed the display screen (the most expensive item, typically) can be used for normal TV show watching or internet activity as well, or for control of the home—if a touch screen. In a standup mode the large screen display depicted in FIGS. 2-4 can be used for various games such as quick draw, charades, etc. the screen or the image on the screen can also be rotated to the horizontal by the user to make a wide screen TV display.

Voice recognition techniques usable with the invention are now being researched in earnest in order to allow the user to interact with computer based functions. IBM VIA VOICE and DRAGON SOFTWARE Naturally Speaking products have already reached the general office market, and are reasonably accurate and effective if the surrounding environment is quiet and stable. More reliable in noisier environments are those specialized limited capability such as Fonix Corporations Automatic Speech Recognition (ASR).

As has been noted above the invention has a value in motivating people to hold to a health plan, diet, exercise, or both. And it may encourage some medication as well. This can be its main or only function, independent of the clothing issue, even though clothes are often the biggest motivator, as that is how the world sees you, and how you want the world to see you.

The video data of ones present or future predicted model, generally fully dressed, can be shared with others over the internet or otherwise. This provides an added degree of motivation, in that one can exchange progress notes with ones friends, as well as with advisors such as weight watcher personnel or fitness trainers, health scientists or doctors. Such data can also be accompanied by actual digital photographs where desired. The expected weight or other measurements of a user in a given regimen or activity, in pounds, kilos or other suitable and understandable units, can be displayed on the screen of the invention along with the digital model portrayed. The various models and regimens can be stored on digital media for further use in the future. The invention can be used as well to predict the future shape and appearance with or without clothes of persons who are on medical regimens, for example drugs with weight or shape changing side effects The invention may also incorporate data as to your past shape, and use that in forming a comparative model, or in aiding further definition of what exercise or dietary plan will achieve a certain future shape. For example consider the apparatus of FIG. 7, which captures two dimensional images of the person, and uses these to generate a two or three dimensional body model. Such images can be obtained from photographs as well, either digital photos or scanned film photos, which can yield dimensional data and relationship including shape parameters.

If for example, if it was known that a person weighed 20 pounds less at some point in time in the past when a picture was taken, and/or had certain measurements taken from either that picture, or known in some other way (which also could be taken from a particular size of clothes for example a size 36 waist trouser on the person) then this data can be used to aid in the prediction of a future body model at different times when the person under took diet or exercise. Such a plan is often indeed undertaken so that the person can "fit into" some clothes bought in the past as a result of undertaking a diet and/or exercise program.

The foregoing discussion should be understood as illustrative and should not be considered to be limiting in any sense. While this invention has been particularly shown and described with references to preferred embodiments thereof, it will be understood by those skilled in the art that various changes in form and details maybe made therein without departing from the spirit and scope of the invention.

What is claimed:

1. A method for assisting a person undertaking an exercise program comprising the steps of:

providing a computer model of at least a portion of the body of said person;

electro-optically monitoring, during exercise, at least one point on said person's body which is affected by said exercise;

using said monitored point, determining a change in said computer model; and dynamically providing information concerning said change to said person while said person is still exercising.

2. A method according to claim 1 wherein an image derived from said changed model is displayed to said person.

3. A method according to claim 2, wherein said image is a 3D image.

4. A method according to claim 1, including the further step of considering medical data concerning said person in providing said information.

5. A method according to claim 1, including the further step of monitoring a heart rate of the person while exercising and providing information relating thereto to said person.

6. A method according to claim 1, including the further step of transmitting said information from a remote location over the internet.

7. A method according to claim 6, wherein said information includes motivational or instructional messages to said person.

8. A method according to claim 1, where said information is provided in response to said person's actions during said exercise.

9. A method according to claim 1, wherein said information includes computer generated motivational or instructional messages to said person.

10. A method according to claim 1, in which said information concerns the safety of said person.

11. A method according to claim 1, further including the step of modifying said information provided at a future time as a result of a change in said monitored exercise by said person.

* * * * *